(12) United States Patent
Van Der Veen et al.

(10) Patent No.: US 9,243,000 B2
(45) Date of Patent: *Jan. 26, 2016

(54) THIA-TRIAZA-INDACENES

(75) Inventors: Lars Van Der Veen, Alsbach-Haehnlein (DE); Darryl McConnell, Vienna (AT); Siegfried Schneider, Vienna (AT); Matthias Grauert, Biberach an der Riss (DE); Andreas Schoop, Neuried (DE); Tobias Wunberg, Hinterbruehl (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 89 days.

This patent is subject to a terminal disclaimer.

(21) Appl. No.: 13/265,241

(22) PCT Filed: Apr. 22, 2010

(86) PCT No.: PCT/EP2010/055321
§ 371 (c)(1),
(2), (4) Date: Dec. 22, 2011

(87) PCT Pub. No.: WO2010/122091
PCT Pub. Date: Oct. 28, 2010

(65) Prior Publication Data
US 2012/0108618 A1 May 3, 2012

(30) Foreign Application Priority Data
Apr. 22, 2009 (EP) .................... 09158494

(51) Int. Cl.
*C07D 513/04* (2006.01)
*A61K 31/381* (2006.01)
*C07D 513/14* (2006.01)

(52) U.S. Cl.
CPC ............ *C07D 513/04* (2013.01); *C07D 513/14* (2013.01)

(58) Field of Classification Search
CPC .......................... C07D 513/04; A61K 31/381
USPC .......................... 548/151; 514/366
See application file for complete search history.

(56) References Cited

FOREIGN PATENT DOCUMENTS

| CA | 2579279 A1 | 4/2006 |
|---|---|---|
| CA | 2579288 A1 | 4/2006 |
| WO | 96/09304 A1 | 3/1996 |
| WO | WO-96/09304 | * 3/1996 |
| WO | WO-9609304 | * 3/1996 |
| WO | 2004104007 A1 | 12/2004 |
| WO | 2006/040279 A1 | 4/2006 |
| WO | 2006/040281 A1 | 4/2006 |

OTHER PUBLICATIONS

U.S. Pat. No. 8,304,556 McConnell et al. (2012).*
U.S. Pat. No. 7,902,183 Steurer et al. (2011).*
U.S. Pat. No. 7,893,049 McConnell et al. (2011).*
STN results for Grauert et al. WO 2007/115933 (2007).*
STN results Breitfelder et al. WO 2006040279 (2006).*
International Search Report, Form PCT/ISA/210, and Written Opinion, Form PCT/ISA/237, for corresponding PCT/EP2010/055321; date of mailing: Jun. 29, 2010.

* cited by examiner

*Primary Examiner* — Scarlett Goon
*Assistant Examiner* — Sonya Wright
(74) *Attorney, Agent, or Firm* — Michael P. Morris; Alan R. Stempel

(57) ABSTRACT

The present invention encompasses compounds of general formula (1) wherein $R^1$ to $R^3$ and X are defined as in claim 1, which are suitable for the treatment of diseases characterized by excessive or abnormal cell proliferation, and the use thereof for preparing a medicament having the above-mentioned properties.

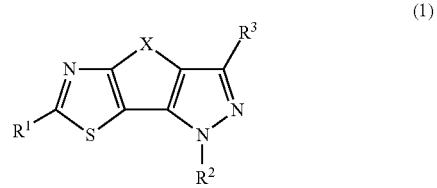

3 Claims, No Drawings

THIA-TRIAZA-INDACENES

The present invention relates to new thia-triaza-indacenes of general formula (1)

(1)

wherein the groups $R^1$ to $R^3$ and X have the meanings given in the claims and specification, the isomers thereof, processes for preparing these thia-triaza-indacenes and their use as medicaments.

BACKGROUND TO THE INVENTION

A number of protein kinases have already proved to be suitable target molecules for therapeutic intervention in a variety of indications, e.g. cancer and inflammatory and autoimmune diseases. Since a high percentage of the genes involved in the development of cancer which have been identified thus far encode kinases, these enzymes are attractive target molecules for the therapy of cancer in particular.

Phosphatidylinositol-3-kinases (PI3-kinases) are a subfamily of the lipid kinases which catalyse the transfer of a phosphate group to the 3'-position of the inositol ring of phosphoinositides.

They play an important role in numerous cell processes such as e.g. cell growth and differentiation processes, the control of cytoskeletal changes and the regulation of intracellular transport processes. On the basis of their in vitro specificity for certain phosphoinositide substrates the PI3-kinases can be divided into different categories.

Thiazolyl-dihydro-indazoles are described for example as kinases inhibiting compounds in WO2006040279 and WO2006040281.

DETAILED DESCRIPTION OF THE INVENTION

It has now surprisingly been found that compounds of general formula (1), wherein the groups $R^1$ to $R^3$ and X have the meanings given below, act as inhibitors of specific kinases. Thus, the compounds according to the invention may be used for example for the treatment of diseases connected with the activity of specific kinases and characterised by excessive or abnormal cell proliferation.

The present invention relates to compounds of general formula (1)

(1)

wherein
X is a substituted C2-alkylidene chain; or
X is an optionally substituted C2-alkylidene chain wherein one or two methylene units are independently from one another replaced by C(O), $NR^gC(O)$, SO, $SO_2$, $NR^gSO_2$, O, S, or $NR^g$; and wherein the substituents are independently from one another selected from $R^f$ and $R^g$; and
$R^1$ denotes hydrogen or $R^4$; and
$R^2$ denotes hydrogen or $R^5$; and
$R^3$ denotes hydrogen or $R^6$; and
each $R^4$, $R^5$ and $R^6$ independently of one another denotes a group selected from among $R^a$, $R^b$ and $R^a$ substituted by one or more identical or different $R^b$ and/or $R^c$; and
each $R^a$ independently of one another denotes a group optionally substituted by one or more identical or different $R^b$ and/or $R^c$, selected from among $C_{1-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl,
each $R^b$ denotes a suitable group and is selected independently of one another from among =O, —$OR^c$, $C_{1-3}$haloalkyloxy, —$OCF_3$, —$OCHF_2$, =S, —$SR^c$, =$NR^c$, =$NOR^c$, =$NNR^cR^c$, =$NN(R^g)C(O)NR^cR^c$, —$NR^cR^c$, —$ONR^cR^c$, —$N(OR^c)R^c$, —$N(R^g)NR^cR^c$, halogen, —$CF_3$, —CN, —NC, —OCN, —SCN, —NO, —$NO_2$, =$N_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)OR^c$, —$C(O)SR^c$, —$C(O)NR^cR^c$, —$C(O)N(R^g)NR^cR^c$, —$C(O)N(R^g)OR^c$, —$C(NR^g)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^g)NR^cR^c$, —$SC(O)R^c$, —$SC(O)OR^c$, —$SC(O)NR^cR^c$, —$SC(NR^g)NR^cR^c$, —$N(R^g)C(O)R^c$, —$N[C(O)R^c]_2$, —$N(OR^g)C(O)R^c$, —$N(R^g)C(NR^g)R^c$, —$N(R^g)N(R^g)C(O)R^c$, —$N[C(O)R^c]NR^cR^c$, —$N(R^g)C(S)R^c$, —$N(R^g)S(O)R^c$, —$N(R^g)S(O)OR^c$, —$N(R^g)S(O)_2R^c$, —$N[S(O)_2R^c]_2$, —$N(R^g)S(O)_2OR^c$, —$N(R^g)S(O)_2NR^cR^c$, —$N(R^g)[S(O)_2]_2R^c$, —$N(R^g)C(O)OR^c$, —$N(R^g)C(O)SR^c$, —$N(R^g)C(O)NR^cR^c$, —$N(R^g)C(O)NR^cOR^c$, —$N(R^g)C(O)NR^gNR^cR^c$, —$N(R^g)N(R^g)C(O)NR^cR^c$, —$N(R^g)C(S)NR^cR^c$, —$[N(R^g)C(O)]_2R^c$, —$N(R^g)[C(O)]_2R^c$, —N{$[C(O)]_2R^c$}$_2$, —$N(R^g)[C(O)]_2OR^c$, —$N(R^g)[C(O)]_2NR^cR^c$, —N{$[C(O)]_2OR^c$}$_2$, —N{$[C(O)]_2NR^cR^c$}$_2$, —$[N(R^g)C(O)]_2OR^c$, —$N(R^g)C(NR^g)OR^c$, —$N(R^g)C(NOH)R^c$, —$N(R^g)C(NR^g)SR^c$, —$N(R^g)C(NR^g)NR^cR^c$, —N=$R^c$ and —N=$C(R^g)NR^cR^c$ and
each $R^c$ independently of one another denotes hydrogen or a group optionally substituted by one or more identical or different $R^d$ and/or $R^e$, selected from among $C_{1-6}$alkyl, $C_{1-6}$alkenyl, $C_{1-6}$alkynyl, 2-6 membered heteroalkyl, $C_{1-6}$haloalkyl, $C_{3-10}$ cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, and
each $R^d$ denotes a suitable group and is selected independently of one another from among =O, —$OR^e$, $C_{1-3}$haloalkyloxy, —$OCF_3$, —$OCHF_2$, =S, —$SR^e$, =$NR^e$, =$NOR^e$, =$NNR^eR^e$, =$NN(R^g)C(O)NR^eR^e$, —$NR^eR^e$, —$ONR^eR^e$, —$N(R^g)NR^eR^e$, halogen, —$CF_3$, —CN, —NC, —OCN, —SCN, —NO, —$NO_2$, =$N_2$, —$N_3$, —$S(O)R^e$, —$S(O)OR^e$, —$S(O)_2R^e$, —$S(O)_2OR^e$, —$S(O)NR^eR^e$, —$S(O)_2NR^eR^e$, —$OS(O)R^e$, —$OS(O)_2R^e$, —$OS(O)_2OR^e$, —$OS(O)NR^eR^e$, —$OS(O)_2NR^eR^e$, —$C(O)R^e$, —$C(O)OR^e$, —$C(O)SR^e$, —$C(O)NR^eR^e$, —$C(O)N(R^g)NR^eR^e$, —C(O)N $(R^g)OR^e$, —$C(NR^g)NR^eR^e$, —$C(NOH)R^e$, —$C(NOH)NR^eR^e$, —$OC(O)R^e$, —$OC(O)OR^e$, —$OC(O)SR^e$, —$OC(O)NR^eR^e$, —$OC(NR^g)NR^eR^e$, —$SC(O)R^e$, —$SC(O)OR^e$, —$SC(O)NR^eR^e$, —$SC(NR^g)NR^eR^e$, —$N(R^g)C(O)R^e$, —$N[C(O)R^e]_2$, —$N(OR^g)C(O)R^e$, —$N(R^g)C(NR^g)R^e$, —$N(R^g)N(R^g)C(O)R^e$, —$N[C(O)R^e]NR^eR^e$, —$N(R^g)C(S)R^e$, —$N(R^g)S(O)R^e$, —$N(R^g)S(O)OR^e$—$N(R^g)S(O)_2R^e$, —$N[S(O)_2R^e]_2$, —$N(R^g)S(O)_2OR^e$, —$N(R^g)S(O)_2NR^eR^e$, —$N(R^g)[S(O)_2]_2R^e$, —$N(R^g)C(O)OR^e$, —$N(R^g)C(O)SR^e$, —$N(R^g)C(O)NR^eR^e$, —$N(R^g)C(O)NR^eOR^e$, —$N(R^g)C(O)NR^gNR^eR^e$, —$N(R^g)N(R^g)C(O)NR^eR^e$, —$N(R^g)C(S)NR^eR^e$, —$[N(R^g)C(O)]_2R^e$, —$N(R^g)[C(O)]_2R^e$, —$N\{[C(O)]_2R^e\}_2$, —$N(R^g)[C(O)]_2OR^e$, —$N(R^g)[C(O)]_2NR^eR^e$, —$N\{[C(O)]_2OR^e\}_2$, —$N\{[C(O)]_2NR^eR^e\}_2$, —$[N(R^g)C(O)]_2OR^e$, —$N(R^g)C(NR^g)OR^e$, —$N(R^g)C(NOH)R^e$, —$N(R^g)C(NR^g)SR^e$, —$N(R^g)C(NR^g)NR^eR^e$, —$N=R^eR^e$ and —$N=C(R^g)NR^eR^e$ each $R^e$ independently of one another denotes hydrogen or a group optionally substituted by one or more identical or different $R^f$ and/or $R^g$, selected from among $C_{1-6}$alkyl, $C_{1-6}$alkenyl, $C_{1-6}$alkynyl, 2-6 membered heteroalkyl, $C_{1-6}$haloalkyl, $C_{3-10}$cyclo alkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, and each $R^f$ denotes a suitable group and in each case is selected independently of one another from among =O, —$OR^g$, $C_{1-3}$haloalkyloxy, —$OCF_3$, —$OCHF_2$, =S, —$SR^g$, =$NR^g$, =$NOR^g$, =$NNR^gR^g$, =$NN(R^h)C(O)NR^gR^g$, —$NR^gR^g$, —$ONR^gR^g$, —$N(R^h)NR^gR^g$, halogen, —$CF_3$, —CN, —NC, —OCN, —SCN, —NO, —$NO_2$, =$N_2$, —$N_3$, —$S(O)R^g$, —$S(O)OR^g$, —$S(O)_2R^g$, —$S(O)_2OR^g$, —$S(O)NR^gR^g$, —$S(O)_2NR^gR^g$, —$OS(O)R^g$, —$OS(O)_2R^g$, —$OS(O)_2OR^g$, —$OS(O)NR^gR^g$, —$OS(O)_2NR^gR^g$, —$C(O)R^g$, —$C(O)OR^g$, —$C(O)SR^g$, —$C(O)NR^gR^g$, —$C(O)N(R^h)NR^gR^g$, —$C(O)N(R^h)OR^g$, —$C(NR^h)NR^gR^g$, —$C(NOH)R^g$, —$C(NOH)NR^gR^g$, —$OC(O)R^g$, —$OC(O)OR^g$, —$OC(O)SR^g$, —$OC(O)NR^gR^g$, —$OC(NR^h)NR^gR^g$, —$SC(O)R^g$, —$SC(O)OR^g$, —$SC(O)NR^gR^g$, —$SC(NR^h)NR^gR^g$, —$N(R^h)C(O)R^g$, —$N[C(O)R^g]_2$, —$N(OR^h)C(O)R^g$, —$N(R^h)C(NR^h)R^g$, —$N(R^h)N(R^h)C(O)R^g$, —$N[C(O)R^g]NR^gR^g$, —$N(R^h)C(S)R^g$, —$N(R^h)S(O)R^g$, —$N(R^h)S(O)OR^g$, —$N(R^h)S(O)_2R^g$, —$N[S(O)_2R^g]_2$, —$N(R^h)S(O)_2OR^g$, —$N(R^h)S(O)_2NR^gR^g$, —$N(R^h)[S(O)_2]_2R^g$, —$N(R^h)C(O)OR^g$, —$N(R^h)C(O)SR^g$, —$N(R^h)C(O)NR^gR^g$, —$N(R^h)C(O)NR^gOR^g$, —$N(R^h)C(O)NR^hNR^gR^g$, —$N(R^h)N(R^h)C(O)NR^gR^g$, —$N(R^h)C(S)NR^gR^g$, —$[N(R^h)C(O)]_2R^g$, —$N(R^h)[C(O)]_2R^g$, —$N\{[C(O)]_2R^g\}_2$, —$N(R^h)[C(O)]_2OR^g$, —$N(R^{11})[C(O)]_2NR^gR^g$, —$N\{[C(O)]_2OR^g\}_2$, —$N\{[C(O)]_2NR^gR^g\}_2$, —$[N(R^h)C(O)]_2OR^g$, —$N(R^h)C(NR^h)OR^g$, —$N(R^h)C(NOH)R^g$, —$N(R^h)C(NR^h)SR^g$, —$N(R^h)C(NR^h)NR^gR^g$, —$N=R^hR^h$ and —$N=C(R^h)NR^hR^h$; and each $R^g$ independently of one another denotes hydrogen or a group optionally substituted by one or more identical or different $R^h$, selected from among $C_{1-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero aryl, 6-18 membered heteroarylalkyl, 3-14 membered heterocycloalkyl and 4-14 membered heterocycloalkylalkyl; and each $R^h$ is selected independently of one another from among hydrogen, $C_{1-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, optionally in the form of the tautomers, the racemates, the enantiomers, the diastereomers, and the mixtures thereof, and optionally the pharmacologically acceptable salts thereof.

One aspect of the invention are compounds of general formula (1), wherein $R^3$ is a radical selected from the group consisting of imidazol, pyrazole, triazol, furyl, oxazolyl, pyridyl, pyrazinyl, pyrimidinyl and pyridazinyl, optionally substituted by one or more $R^6$.

A further aspect of the invention are compounds of general formula (1), wherein $R^3$ is pyridyl, optionally substituted by one or more $R^6$.

A further aspect of the invention are compounds of general formula (1), wherein $R^3$ is selected from —$C(O)R^c$, —$C(O)OR^c$ and —$C(O)NR^cR^c$.

A further aspect of the invention are compounds of general formula (1), wherein $R^1$ is selected from among —$NHR^c$, —$NHC(O)R^c$, —$NHC(O)OR^c$, —$NHC(O)NR^cR^c$ and —$NHC(O)N(R^g)OR^c$.

A further aspect of the invention are compounds of general formula (1), wherein $R^2$ is selected from among $C_{1-6}$alkyl, $C_{1-6}$alkenyl, $C_{1-6}$alkynyl, $C_{3-10}$cycloalkyl, $C_{6-10}$aryl, $C_{7-16}$arylalkyl, 5-12 membered Heteroaryl, 6-18 membered heteroarylalkyl, 3-14 membered heterocycloalkyl and 4-14 membered heterocycloalkylalkyl, optionally substituted by one or more $R^5$.

A further aspect of the invention are compounds of general formula (1), wherein X is a substituted C2 alkylidene chain.

A further aspect of the invention are compounds of general formula (1), wherein X is an optionally substituted C2 alkylidene chain, wherein one methylene unit is replaced by O or S.

A further aspect of the invention are compounds of general formula (1)—or the pharmaceutically active salts thereof—for use as a medicament.

A further aspect of the invention are compounds of general formula (1)—or the pharmacologically effective salts thereof, for preparing a medicament with an antiproliferative activity.

A further aspect of the invention is a pharmaceutical preparation, containing as active substance one or more compounds of general formula (1) or the physiologically acceptable salts thereof optionally in conjunction with conventional excipients and/or carriers.

A further aspect of the invention is the use of a compound of general formula (1) for preparing a pharmaceutical composition for the treatment and/or prevention of cancer, infections, inflammatory and autoimmune diseases.

A further aspect of the invention is a pharmaceutical preparation comprising a compound of general formula (1) and at least one other cytostatic or cytotoxic active substance, different from formula (1), optionally in the form of the tautomers, the racemates, the enantiomers, the diastereomers and the mixtures thereof, and optionally the pharmacologically acceptable acid addition salts thereof.

A further aspect of the invention are compounds of general formula (1A), (1B) or (1C)

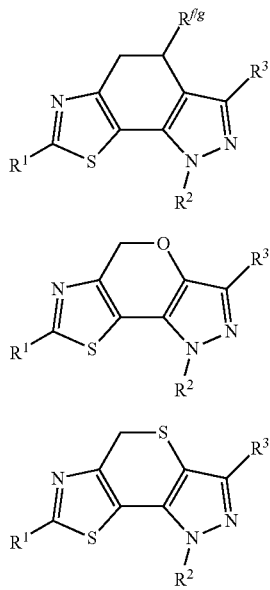

(1A)

(1B)

(1C)

wherein
R¹ denotes hydrogen or R⁴; and
R² denotes hydrogen or R⁵; and
R³ denotes hydrogen or R⁶; and
each R⁴, R⁵ and R⁶ independently of one another denotes a group selected from among $R^a$, $R^b$ and $R^a$ substituted by one or more identical or different $R^b$ and/or $R^c$; and
each $R^a$ independently of one another denotes a group optionally substituted by one or more identical or different $R^b$ and/or $R^c$, selected from among $C_{1-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^b$ denotes a suitable group and is selected independently of one another from among =O, —OR$^c$, $C_{1-3}$haloalkyloxy, —OCF$_3$, —OCHF$_2$, =S, —SR$^c$, =NR$^c$, =NOR$^c$, =NNR$^c$R$^c$, =NN(R$^g$)C(O)NR$^c$R$^c$, —NR$^c$R$^c$, —ONR$^c$R$^c$, —N(OR$^c$)R$^c$, —N(R$^g$)NR$^c$R$^c$, halogen, —CF$_3$, —CN, —NC, —OCN, —SCN, —NO, —NO$_2$, =N$_2$, —N$_3$, —S(O)R$^c$, —S(O)OR$^c$, —S(O)$_2$R$^c$, —S(O)$_2$OR$^c$, —S(O)NR$^c$R$^c$, —S(O)$_2$NR$^c$R$^c$, —OS(O)R$^c$, —OS(O)$_2$R$^c$, —OS(O)$_2$OR$^c$, —OS(O)NR$^c$R$^c$, —OS(O)$_2$NR$^c$R$^c$, —C(O)R$^c$, —C(O)OR$^c$, —C(O)SR$^c$, —C(O)NR$^c$R$^c$, —C(O)N(R$^g$)NR$^c$R$^c$, —C(O)N(R$^g$)OR$^c$, —C(NR$^g$)NR$^c$R$^c$, —C(NOH)R$^c$, —C(NOH)NR$^c$R$^c$, —OC(O)R$^c$, —OC(O)OR$^c$, —OC(O)SR$^c$, —OC(O)NR$^c$R$^c$, —OC(NR$^g$)NR$^c$R$^c$, —SC(O)R$^c$, —SC(O)OR$^c$, —SC(O)NR$^c$R$^c$, —SC(NR$^g$)NR$^c$R$^c$, —N(R$^g$)C(O)R$^c$, —N[C(O)R$^c$]$_2$, —N(OR$^g$)C(O)R$^c$, —N(R$^g$)C(NR$^g$)R$^c$, —N(R$^g$)N(R$^g$)C(O)R$^c$, —N[C(O)R$^c$]NR$^c$R$^c$, —N(R$^g$)C(S)R$^c$, —N(R$^g$)S(O)R$^c$, —N(R$^g$)S(O)OR$^c$, —N(R$^g$)S(O)$_2$R$^c$, —N[S(O)$_2$R$^c$]$_2$, —N(R$^g$)S(O)$_2$OR$^c$, —N(R$^g$)S(O)$_2$NR$^c$R$^c$, —N(R$^g$)[S(O)$_2$]$_2$R$^c$, —N(R$^g$)C(O)OR$^c$, —N(R$^g$)C(O)SR$^c$, —N(R$^g$)C(O)NR$^c$R$^c$, —N(R$^g$)C(O)NR$^c$OR$^c$, —N(R$^g$)C(O)NR$^g$NR$^c$R$^c$, —N(R$^g$)N(R$^g$)C(O)NR$^c$R$^c$, —N(R$^g$)C(S)NR$^c$R$^c$, —[N(R$^g$)C(O)]$_2$R$^c$, —N(R$^g$)[C(O)]$_2$R$^c$, —N{[C(O)]$_2$R$^c$}$_2$, —N(R$^g$)[C(O)]$_2$OR$^c$, —N(R$^g$)[C(O)]$_2$NR$^c$R$^c$, —N{[C(O)]$_2$OR$^c$}$_2$, —N{[C(O)]$_2$NR$^c$R$^c$}$_2$, —[N(R$^g$)C(O)]$_2$OR$^c$, —N(R$^g$)C(NR$^g$)OR$^c$, —N(R$^g$)C(NOH)R$^c$, —N(R$^g$)C(NR$^g$)SR$^c$, —N(R$^g$)C(NR$^g$)NR$^c$R$^c$, —N=R$^c$ and —N=C(R$^g$)NR$^c$R$^c$ and each R$^c$ independently of one another denotes hydrogen or a group optionally substituted by one or more identical or different R$^d$ and/or R$^e$, selected from among $C_{1-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, and each R$^d$ denotes a suitable group and is selected independently of one another from among =O, —OR$^e$, $C_{1-3}$haloalkyloxy, —OCF$_3$, —OCHF$_2$, =S, —SR$^e$, =NR$^e$, =NOR$^e$, =NNR$^e$R$^e$, =NN(R$^g$)C(O)NR$^e$R$^e$, —NR$^e$R$^e$, —ONR$^e$R$^e$, —N(R$^g$)NR$^e$R$^e$, halogen, —CF$_3$, —CN, —NC, —OCN, —SCN, —NO, —NO$_2$, =N$_2$, —N$_3$, —S(O)R$^e$, —S(O)OR$^e$, —S(O)$_2$R$^e$, —S(O)$_2$OR$^e$, —S(O)NR$^e$R$^e$, —S(O)$_2$NR$^e$R$^e$, —OS(O)R$^e$, —OS(O)$_2$R$^e$, —OS(O)$_2$OR$^e$, —OS(O)NR$^e$R$^e$, —OS(O)$_2$NR$^e$R$^e$, —C(O)R$^e$, —C(O)OR$^e$, —C(O)SR$^e$, —C(O)NR$^e$R$^e$, —C(O)N(R$^g$)NR$^e$R$^e$, —C(O)N(R$^g$)OR$^e$, —C(NR$^g$)NR$^e$R$^e$, —C(NOH)R$^e$, —C(NOH)NR$^e$R$^e$, —OC(O)R$^e$, —OC(O)OR$^e$, —OC(O)SR$^e$, —OC(O)NR$^e$R$^e$, —OC(NR$^g$)NR$^e$R$^e$, —SC(O)R$^e$, —SC(O)OR$^e$, —SC(O)NR$^e$R$^e$, —SC(NR$^g$)NR$^e$R$^e$, —N(R$^g$)C(O)R$^e$, —N[C(O)R$^e$]$_2$, —N(OR$^g$)C(O)R$^e$, —N(R$^g$)C(NR$^g$)R$^e$, —N(R$^g$)N(R$^g$)C(O)R$^e$, —N[C(O)R$^e$]NR$^e$R$^e$, —N(R$^g$)C(S)R$^e$, —N(R$^g$)S(O)R$^e$, —N(R$^g$)S(O)OR$^e$, —N(R$^g$)S(O)$_2$R$^e$, —N[S(O)$_2$R$^e$]$_2$, —N(R$^g$)S(O)$_2$OR$^e$, —N(R$^g$)S(O)$_2$NR$^e$R$^e$, —N(R$^g$)[S(O)$_2$]$_2$R$^e$, —N(R$^g$)C(O)OR$^e$, —N(R$^g$)C(O)SR$^e$, —N(R$^g$)C(O)NR$^e$R$^e$, —N(R$^g$)C(O)NR$^e$OR$^e$, —N(R$^g$)C(O)NR$^g$NR$^e$R$^e$, —N(R$^g$)N(R$^g$)C(O)NR$^e$R$^e$, —N(R$^g$)C(S)NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$OR$^e$, —N(R$^g$)[C(O)]$_2$NR$^e$R$^e$, —N{[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, —N(R$^g$)C(NOH)R$^e$, —N(R$^g$)C(NR$^g$)SR$^e$, —N(R$^g$)C(NR$^g$)NR$^e$R$^e$, —N=R$^e$ and —N=C(R$^g$)NR$^e$R$^e$ each R$^e$ independently of one another denotes hydrogen or a group optionally substituted by one or more identical or different R$^f$ and/or R$^g$, selected from among $C_{1-6}$alkyl, $C_{1-6}$alkenyl, $C_{1-6}$alkynyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, and each R$^f$ denotes a suitable group and in each case is selected independently of one another from among =O, —OR$^g$, $C_{1-3}$haloalkyloxy, —OCF$_3$, —OCHF$_2$, =S, —SR$^g$, =NR$^g$, =NOR$^g$, =NNR$^g$R$^g$, =NN(R$^h$)C(O)NR$^g$R$^g$, —NR$^g$R$^g$, —ONR$^g$R$^g$, —N(R$^h$)NR$^g$R$^g$, halogen, —CF$_3$, —CN, —NC, —OCN, —SCN, —NO, —NO$_2$, =N$_2$, —N$_3$, —S(O)R$^g$, —S(O)OR$^g$, —S(O)$_2$R$^g$, —S(O)$_2$OR$^g$, —S(O)NR$^g$R$^g$, —S(O)$_2$NR$^g$R$^g$, —OS(O)R$^g$, —OS(O)$_2$R$^g$, —OS(O)$_2$OR$^g$, —OS(O)NR$^g$R$^g$, —OS(O)$_2$NR$^g$R$^g$, —C(O)R$^g$, —C(O)OR$^g$, —C(O)SR$^g$, —C(O)NR$^g$R$^g$, —C(O)N(R$^h$)NR$^g$R$^g$, —C(O)N(R$^h$)OR$^g$, —C(NR$^h$)NR$^g$R$^g$, —C(NOH)R$^g$, —C(NOH)NR$^g$R$^g$, —OC(O)R$^g$, —OC(O)OR$^g$, —OC(O)SR$^g$, —OC(O)NR$^g$R$^g$, —OC(NR$^h$)NR$^g$R$^g$, —SC(O)R$^g$, —SC(O)OR$^g$, —SC(O)NR$^g$R$^g$, —SC(NR$^h$)NR$^g$R$^g$, —N(R$^h$)C(O)R$^g$, —N[C(O)R$^g$]$_2$, —N(OR$^h$)C(O)R$^g$, —N(R$^h$)C(NR$^h$)R$^g$, —N(R$^h$)N(R$^h$)C(O)R$^g$, —N[C(O)R$^g$]NR$^g$R$^g$, —N(R$^h$)C(S)R$^g$, —N(R$^h$)S(O)R$^g$, —N(R$^h$)S(O)OR$^g$, —N(R$^h$)S(O)$_2$R$^g$, —N[S(O)$_2$R$^g$]$_2$, —N(R$^h$)S(O)$_2$OR$^g$, —N(R$^h$)S(O)$_2$NR$^g$R$^g$, —N(R$^h$)[S(O)$_2$]$_2$R$^g$, —N(R$^h$)C(O)OR$^g$, —N(R$^h$)C(O)SR$^g$, —N(R$^h$)C(O)NR$^g$R$^g$, —N(R$^h$)C(O)NR$^g$OR$^g$, —N(R$^h$)C(O)NR$^h$NR$^g$R$^g$, —N(R$^h$)N(R$^h$)C(O)NR$^g$R$^g$, —N(R$^h$)C(S)NR$^g$R$^g$, —[N(R$^h$)C(O)]$_2$R$^g$, —N(R$^h$)[C(O)]$_2$R$^g$, —N{

[C(O)]$_2$R$^g$}$_2$, —N(R$^h$)[C(O)]$_2$OR$^g$, —N(R$^{11}$)[C(O)]$_2$NR$^g$R$^g$, —N{[C(O)]$_2$OR$^g$}$_2$, —N{[C(O)]$_2$NR$^g$R$^g$}$_2$, —[N(R$^h$)C(O)]$_2$OR$^g$, —N(R$^h$)C(NR$^h$)OR$^g$, —N(R$^h$)C(NOH)R$^g$, —N(R$^h$)C(NR$^h$)SR$^g$, —N(R$^h$)C(NR$^h$)NR$^g$R$^g$, —N=R$^h$R$^h$ and —N=C(R$^h$)NR$^h$R$^h$; and each R$^g$ independently of one another denotes hydrogen or a group optionally substituted by one or more identical or different R$^h$, selected from among C$_{1-6}$alkyl, C$_{1-6}$alkenyl, C$_{1-6}$alkynyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero aryl, 6-18 membered heteroarylalkyl, 3-14 membered heterocycloalkyl and 4-14 membered heterocycloalkylalkyl; and each R$^h$ is selected independently of one another from among hydrogen, C$_{1-6}$alkyl, C$_{1-6}$alkenyl, C$_{1-6}$alkynyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl, optionally in the form of the tautomers, the racemates, the enantiomers, the diastereomers, and the mixtures thereof, and optionally the pharmacologically acceptable salts thereof.

One aspect of the invention are compounds of general formula (1A), (1B) or (1C), wherein R$^3$ is a radical selected from the group consisting of imidazol, pyrazole, triazol, furyl, oxazolyl, pyridyl, pyrazinyl, pyrimidinyl and pyridazinyl, optionally substituted by one or more R$^6$.

A further aspect of the invention are compounds of general formula (1A), (1B) or (1C), wherein R$^3$ is pyridyl, optionally substituted by one or more R$^6$.

A further aspect of the invention are compounds of general formula (1A), (1B) or (1C), wherein R$^3$ is selected from —C(O)R$^c$, —C(O)OR$^c$ and —C(O)NR$^c$R$^c$.

A further aspect of the invention are compounds of general formula (1A), (1B) or (1C), wherein R$^1$ is selected from among —NHR$^c$, —NHC(O)R$^c$, —NHC(O)OR$^c$, —NHC(O)NR$^c$R$^c$ and —NHC(O)N(R$^g$)OR$^c$.

A further aspect of the invention are compounds of general formula (1A), (1B) or (1C), wherein R$^2$ is selected from among C$_{1-6}$alkyl, C$_{3-10}$cycloalkyl, C$_{6-10}$aryl, C$_{7-16}$arylalkyl, 5-12 membered Heteroaryl, 6-18 membered heteroarylalkyl, 3-14 membered heterocycloalkyl and 4-14 membered heterocycloalkylalkyl, optionally substituted by one or more R$^5$.

A further aspect of the invention are compounds of general formula 1A), (1B) or (1C)—or the pharmaceutically active salts thereof—for use as a medicament.

A further aspect of the invention are compounds of general formula 1A), (1B) or (1C)— or the pharmacologically effective salts thereof—for preparing a medicament with an antiproliferative activity.

A further aspect of the invention is a pharmaceutical preparation, containing as active substance one or more compounds of general formula (1A), (1B) or (1C) or the physiologically acceptable salts thereof optionally in conjunction with conventional excipients and/or carriers.

A further aspect of the invention is the use of a compound of general formula (1A), (1B) or (1C) for preparing a pharmaceutical composition for the treatment and/or prevention of cancer, infections, inflammatory and autoimmune diseases.

A further aspect of the invention is a pharmaceutical preparation comprising a compound of general formula (1A), (1B) or (1C) and at least one other cytostatic or cytotoxic active substance, different from formula (1A), (1B) or (1C), optionally in the form of the tautomers, the racemates, the enantiomers, the diastereomers and the mixtures thereof, and optionally the pharmacologically acceptable acid addition salts thereof.

The following Examples illustrate the present invention without restricting its scope.

Intermediates A

General Procedure A1: Formation of Diketones from Acid Chlorides.

The monoketone is added to dry THF (e.g. 10 mmol in 90 mL solvent) and the suspension is cooled to −78° C. under inert atmosphere. LiHMDS (3.4 eq.) is slowly added to the reaction mixture so that the reaction temperature is kept below −60° C. After completion of the addition, a solution of the acid chloride (1.2 eq.) in dry THF (about 2-2.5 M) is added slowly. The reaction mixture is stirred overnight allowing it to warm to RT. For the workup the mixture is cooled to −20° C. and the reaction is quenched with diluted hydrochloric acid and phosphate buffer (22 g NaH$_2$PO$_4$, 87 g Na$_2$HPO$_4$, 530 mL H$_2$O) resulting in a final pH of about 6. Ethyl acetate is added and the organic layer is separated. The aqueous phase is extracted three times with ethyl acetate, the combined organic phases are dried over MgSO$_4$, filtered and the solvent is removed under reduced pressure. The remaining solid is triturated with MTBE. The product may be used without further purification.

General Procedure A2: Formation of Diketones from Esters

The monoketone (1.0 eq.) is dissolved in DMSO (1 M solution) and NaOtBu or sodium tert.-pentoxide (3.0 eq.) is slowly added. The reaction mixture is stirred for 30 min at RT before the ester (1.1 eq.) is added slowly. After completion of the addition the mixture is stirred for 4 h at RT, poured on ice and neutralized with saturated ammonium chloride solution. The precipitate is filtered off, washed with water and dried under vacuum at 40° C. overnight. Alternatively, the solvent is evaporated after completion of the reaction and the crude product may be used for the next step without further purification.

General Procedure A3: Formation of Diketones from Active Esters.

a) Formation of the Active Ester

Carboxylic acid (1.0 eq.) is dissolved in CH$_2$Cl$_2$, CDI (1.0 eq.) is added and the reaction mixture is stirred at RT over night. The solvent is removed in vacuo and the crude product is used without further purification.

b) Formation of the Diketone

A 1 M solution of LiHMDS (3.e eq.) in THF is diluted with THF and the resulting solution is cooled to −10° C. under inert atmosphere. The monoketone (1.0 eq.) is added in small portions so that the reaction temperature is kept below −10° C. After stirring one additional hour at −10° C., a solution of the active ester (2.0 eq.) in THF is added slowly. The reaction mixture is stirred over night allowing it to warm to RT. The reaction is quenched with a saturated solution of NH$_4$Cl in water and the aqueous phase is extracted twice with CH$_2$Cl$_2$. The combined organic layers are dried over MgSO$_4$, filtered and the solvent is removed under reduced pressure. The product is purified by NP- or RP-chromatography.

General Procedure A4: Nucleophilic Aromatic Substitution of o-Fluoropyridines.

The o-fluoropyridine and an excess of the amine are dissolved in EtOH or iPrOH/THF (0.1-0.2 M) and the mixture is heated in the microwave at 100° C. for 30-60 min or alternatively the reaction mixture is stirred at RT for 1-16 h. After completion of the reaction the solvent is removed in vacuo

A-01) 2-Amino-5,5-dimethyl-5,6-dihydro-4H-benzothiazol-7-one

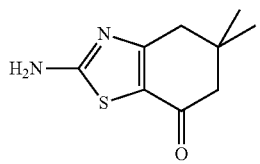

5,5-Dimethyl-cyclohexane-1,3-dione (201 g, 1.43 mol) and NaOAc (176 g, 2.14 mol) are suspended in AcOH (2 L) and Br$_2$ (229 g, 1.43 mol) is added in dropwise while maintaining the reaction temperature between 15 and 20° C. After complete addition, the reaction is stirred at RT overnight. Thiourea (109 g, 1.43 mol) is added in portions and the reaction mixture is heated at 100° C. for 1 h. After cooling to RT, the AcOH is removed in vacuo and the resulting crude product is diluted with water (1 L) and neutralized with an aqueous saturated NaHCO$_3$ solution. The resulting mixture is extracted with ethyl acetate (4×500 mL). The organic layer is washed with brine (500 mL), dried over anhydrous Na$_2$SO$_4$ and the solvent is evaporated in vacuo to give crude product. The crude product is washed with water (1.5 L) to yield 2-amino-5,5-dimethyl-5,6-dihydro-4H-benzothiazol-7-one (211 g, 75% yield).

$^1$H NMR: (400 MHz, DMSO-d$_6$) δ 5.69 (br s, 2H), 2.61 (s, 2H), 2.33 (s, 2H), 1.06 (s, 6H).

A-02) 3-(5,5-Dimethyl-7-oxo-4,5,6,7-tetrahydro-benzothiazol-2-yl)-1,1-dimethyl-urea

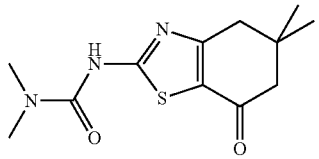

To a solution of 2-amino-5,5-dimethyl-5,6-dihydro-4H-benzothiazol-7-one (151 g, 0.768 mol) in acetonitrile (5 L) are added CDI (249 g, 1.53 mol) and DBU (233 g, 1.53 mol). The reaction mixture is stirred overnight at 100° C. Dimethylamine (310 g, 3.83 mol) is added at RT and the stirring is continued overnight at 100° C. After cooling to RT, the reaction mixture is concentrated in vacuo and the residue is poured into ice water. The pH of the mixture is adjusted to pH 5 with HCl (6 M). The aqueous mixture is extracted with ethyl acetate (4×500 mL). The combined organic layers are washed with brine (500 mL) and dried over anhydrous Na$_2$SO$_4$. The solvent is evaporated in vacuo to give crude product. The crude product is washed with water to give 3-(5,5-dimethyl-7-oxo-4,5,6,7-tetrahydro-benzothiazol-2-yl)-1,1-dimethyl-urea (169 g, 82% yield).

$^1$H NMR: (400 MHz, DMSO-d$_6$) δ 11.28 (br s, 1H), 2.92 (s, 6H), 2.68 (s, 2H), 2.32 (s, 2H), 1.06 (s, 6H).

A-03) N-(5,5-Dimethyl-7-oxo-4,5,6,7-tetrahydro-benzothiazol-2-yl)-acetamide

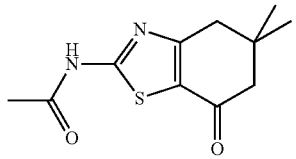 [SMILES: CC(=O)Nc1nc2c(s1)C(=O)CC(C)(C)C2]

2-Amino-5,5-dimethyl-5,6-dihydro-4H-benzothiazol-7-one (40.5 g, 0.206 mol) and Ac$_2$O (400 mL) are heated at 100° C. for 4 h. After cooling to RT, the reaction mixture is concentrated in vacuo. The precipitated solid is collected by filtration and affords N-(5,5-dimethyl-7-oxo-4,5,6,7-tetrahydro-benzothiazol-2-yl)-acetamide (36.5 g, 75% yield).

$^1$H NMR: (400 MHz, DMSO-d$_6$) δ 12.54 (br s, 1H), 2.73 (s, 2H), 2.36 (s, 2H), 2.14 (s, 3H), 1.01 (s, 6H).

A-04) 2-Amino-5-methyl-5,6-dihydro-4H-benzothiazol-7-one

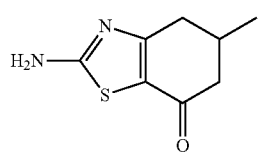

A-04A) 2-Hydroxy-6-methyl-4-oxo-cyclohex-1-enecarboxylic acid methyl ester

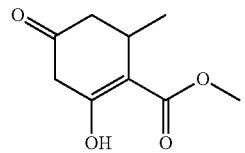

To a freshly prepared solution of MeONa (432 g, 7.99 mol) in MeOH (2 L) is added 3-oxo-butyric acid ethyl ester (1.04 kg, 7.99 mol) over 15 min and the mixture is stirred on an ice bath for an additional 15 min. But-2-enoic acid ethyl ester (912 g, 7.99 mol) is added dropwise at RT and the mixture stirred at RT for 1 h and then the reaction mixture is refluxed for 2 h. After cooling to RT, the precipitated solids are filtered off, dissolved in cold water (1.5 L), acidified with HCl (3 M) to pH to 7 and the resulting mixture is extracted with EtOAc (4×800 mL). The combined organic phase is dried over anhydrous Na$_2$SO$_4$, the solvents are evaporated in vacuo and the residue recrystallized from hexane to give 2-hydroxy-6-methyl-4-oxo-cyclohex-1-enecarboxylic acid methyl ester (672 g, 42% yield).

$^1$H NMR: (400 MHz, DMSO-d$_6$) δ 11.39 (br s, 1H), 5.20 (s, 1H), 3.62 (s, 3H), 3.10-3.08 (m, 1H), 2.35-2.20 (m, 3H), 0.930 (d, J=6.4 Hz, 3H).

A-04B) 5-Methyl-cyclohexane-1,3-dione

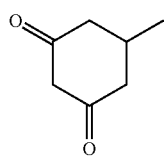

2-Hydroxy-6-methyl-4-oxo-cyclohex-1-enecarboxylic acid methyl ester (600 g, 3.30 mol) is dissolved in NaOH solution (5 M, 3 L) and the solution is refluxed for 2 h. After cooling to RT, the mixture is acidified with H$_2$SO$_4$ (5 M) to pH 7 and extracted with EtOAc (4×1 L). The organic phase is washed with brine and dried over anhydrous Na$_2$SO$_4$. The solvent is evaporated and the residue is recrystallized from hexane to give 5-methyl-cyclohexane-1,3-dione (200 g, 49% yield).

$^1$H NMR: (400 MHz, DMSO-d$_6$) δ 10.94 (br s, 1H), 5.14 (s, 1H), 2.30-2.18 (m, 2H), 2.15-1.96 (m, 3H), 0.95 (d, J=6.4 Hz, 3H).

5-Methyl-cyclohexane-1,3-dione (70.0 g, 0.555 mol) and NaOAc (68.3 g, 0.832 mol) are suspended in AcOH (700 mL) and Br$_2$ (88.7 g, 0.555 mol) is added drop-wise while maintaining the reaction temperature between 15 and 20° C. After complete addition, the reaction is stirred at RT overnight. Thiourea (42.2 g, 0.555 mol) is added in portions and the reaction mixture is heated to 100° C. for 1 h. After cooling to RT, the AcOH is removed in vacuo. The resulting crude product is diluted with water (1 L), adjusted to pH=7 with NaHCO$_3$ solution (3 M) and the resulting mixture is extracted with EtOAc (3×1 L). The organic phase is washed with brine and dried over anhydrous Na$_2$SO$_4$. The solvent is evaporated in vacuo and the residue is recrystallized from hexane to give 2-amino-5-methyl-5,6-dihydro-4H-benzothiazol-7-one (87.2 g, 86% yield).

$^1$H NMR: (400 MHz, DMSO-d$_6$) δ 8.09 (br s, 2H), 2.77-2.72 (m, 1H), 2.39-2.13 (m, 4H), 1.03 (d, J=6.0 Hz, 3H).

A-05) 1,1-Dimethyl-3-(5-methyl-7-oxo-4,5,6,7-tetrahydro-benzothiazol-2-yl)-urea

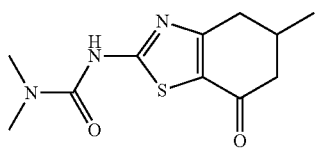

To a solution of 2-amino-5-methyl-5,6-dihydro-4H-benzothiazol-7-one (30.0 g, 0.165 mol) in MeCN (750 mL) are added DBU (75.2 g, 0.495 mol) and CDI (80.1 g, 0.495 mol) at RT. The reaction mixture is stirred at 110° C. overnight. Dimethylamine (93.5 g, 1.15 mol) and another portion of DBU (175 g, 1.15 mol) are added to the mixture at RT and the stirring is continued overnight at 110° C. After cooling to RT, the reaction mixture is evaporated in vacuo and the residue is poured into ice water. The reaction mixture is treated with HCl (6 M) to pH to 5. The aqueous mixture is extracted with EtOAc (3×300 mL). The combined organic phase is washed with brine and dried over anhydrous Na$_2$SO$_4$. The solvent is evaporated and the residue is recrystallized from hexane to give 1,1-dimethyl-3-(5-methyl-7-oxo-4,5,6,7-tetrahydro-benzothiazol-2-yl)-urea (32.1 g, 77% yield).

$^1$H NMR: (400 MHz, DMSO-d$_6$) δ 11.38 (s, 1H), 2.86 (s, 6H), 2.85-2.84 (m, 1H), 2.54-2.26 (m, 4H), 1.07 (d, J=6.0 Hz, 3H).

A-06) N-(5-Methyl-7-oxo-4,5,6,7-tetrahydro-benzothiazol-2-yl)-acetamide

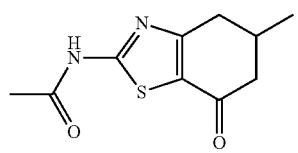

A solution of 2-amino-5-methyl-5,6-dihydro-4H-benzothiazol-7-one (25.0 g, 0.137 mol) in Ac$_2$O (300 mL) is heated at reflux temperature for 3 h. The reaction mixture is then cooled to RT and the precipitate is filtered off to afford N-(5-methyl-7-oxo-4,5,6,7-tetrahydro-benzothiazol-2-yl)-acetamide. Yield: 26 g.

$^1$H NMR: (400 MHz, DMSO-d$_6$) δ 12.56 (s, 1H), 2.95-2.91 (m, 1H), 2.58-2.30 (m, 5H), 2.17 (s, 3H), 1.07 (d, J=6.0 Hz, 3H).

A-07) 2-Amino-5-spirocyclopropyl-5,6-dihydro-4H-benzothiazol-7-one

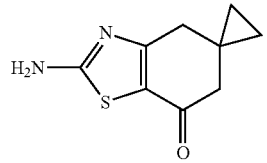 [SMILES: Nc1nc2c(s1)C(=O)CC1(CC1)C2]

The title compound is prepared analogously to 2-amino-5-methyl-5,6-dihydro-4H-benzothiazol-7-one using spiro[2.5]octane-5,7-dione (DE 102004061001) as starting material. HPLC-MS: t$_R$=0.43 min, (M+H)$^+$=195.

A-08) 6-(tert-Butoxycarbonyl-ethyl-amino)-nicotinic acid

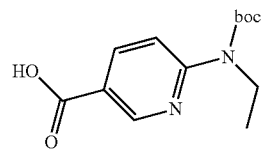

6-Chloro-nicotinic acid methyl ester (60 g, 0.35 mol) is taken up in 500 mL 2 M ethylamine in THF and stirred at 100° C. in a sealed tube for 16 h. The reaction mixture is cooled to RT and the solvents are removed under reduced pressure. The residue is poured on ice and stirred for 15 min. The precipitate is filtered off, washed with water and dried in vacuo. The dried 6-ethylamino-nicotinic acid methyl ester (30 g, 0.17 mol) is dissolved in 150 mL DCM and triethylamine (29 mL, 0.20 mol), DMAP (4.0 g, 33 mmol) and BOC anhydride (100 mL, 0.42 mol) are added successively at 0° C. The reaction mixture is allowed to warm up to RT and stirred for 16 h. To the reaction mixture 100 mL of 10% citric acid in water is added and the reaction mixture is stirred for 10 min. The organic phase is separated, dried over $Na_2SO_4$ and concentrated under reduced pressure.

Yield: 60 g.

The crude 6-(tert-butoxycarbonyl-ethyl-amino)-nicotinic acid methyl ester is taken up in 100 mL dioxane and a solution of lithium hydroxide monohydrate (13.5 g, 0.32 mol) in 100 mL water is added and the reaction mixture is stirred at RT for 4 h. The dioxane is removed from the reaction mixture under reduced pressure, additional water is added and the reaction mixture is acidified to pH 6 with a solution of 10% citric acid in water. The formed precipitate is filtered off and dried in vacuo. Yield: 36 g.

$^1$H NMR (DMSO-$d_6$): δ 13.2 (s, 1H), 8.8 (s, 1H), 8.2 (d, 1H), 7.8 (d, 1H), 4.0 (quart, 2H), 1.5 (s, 9H), 1.2 (t, 3H).

A-09) (5-Chlorocarbonyl-pyridin-2-yl)-ethyl-carbamic acid tert-butyl ester

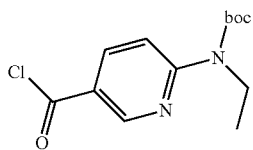

6-(tert-Butoxycarbonyl-ethyl-amino)-nicotinic acid (6.40 g, 24.0 mmol) is taken up in 150 mL DCE, 1-chloro-N,N-2-trimethylpropenyl-amine (6.42 mL, 48.1 mmol) is added and the reaction mixture is stirred overnight at RT. The reaction mixture is concentrated under reduced pressure and the crude product is used in the next step without purification.

A-10) (5-Chlorocarbonyl-pyridin-2-yl)-methyl-carbamic acid tert-butyl ester

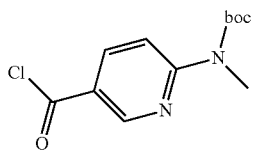

6-(tert-Butoxycarbonyl-methyl-amino)-nicotinic acid (12.5 g, 47.0 mmol) (prepared analogously to A-08 using methyl amine instead of ethylamine) is taken up in 300 mL DCE, 1-chloro-N,N-2-trimethylpropenyl-amine (10.0 mL, 74.8 mmol) is added and the reaction mixture is stirred overnight at RT. The reaction mixture is concentrated under reduced pressure and the crude product is used in the next step without purification.

A-11) 6-[N,N-Di-(tert-Butoxycarbonyl)-amino]-nicotinic acid

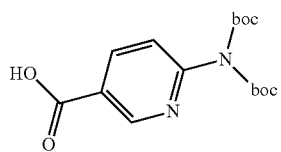

6-Amino-nicotinic acid methyl ester (13.7 g, 90.0 mmol), triethyl amine (12.5 mL, 90.0 mmol) and DMAP (3.30 g, 27.0 mmol) are taken up in 200 mL DCM and a solution of di-tert-butyl dicarbonate (41.3 g, 189 mmol) in 40 mL DCM is added drop wise. The reaction mixture is stirred overnight at RT. An aqueous 5% $KHSO_4$ solution is added and the reaction mixture is extracted with DCM. The combined organic phases are washed with an aqueous 50% saturated $KHCO_3$ solution, dried over $MgSO_4$ and concentrated under reduced pressure. Yield: 34.9 g.

Of this residue 17.3 g is taken up in a mixture of 150 mL MeOH and 300 mL water, lithium hydroxide (2.33 g, 97.3 mmol) is added and the reaction mixture is stirred for 3 h at RT. The reaction mixture is acidified to pH 4 with acetic acid and the formed precipitate is filtered off, washed with water and dried in vacuo. Yield: 11.8 g.

$^1$H NMR (DMSO-$d_6$): δ 9.0 (s, 1H), 8.2 (d, 1H), 7.2 (d, 2H), 1.4 (s, 18H).

A-12) N-tert-Butoxycarbonyl-(5-chlorocarbonyl-pyridin-2-yl)-carbamic acid tert-butyl ester

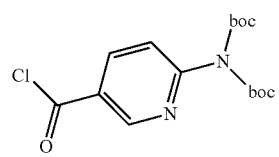

6-[N,N-Di-(tert-butoxycarbonyl)-amino]-nicotinic acid (5.00 g, 14.8 mmol) is dried by azeotropic distillation with toluene and then taken up in 20 mL dry THF and cooled to 0° C. 1-Chloro-N,N-2-trimethylpropenyl-amine (3.95 g, 30.0 mmol) is added drop wise and the reaction mixture is stirred at RT for 3 h. The reaction mixture is concentrated under reduced pressure and the crude product is used in the next step without purification.

A-13) [5-(2-Acetylamino-5-methyl-7-oxo-4,5,6,7-tetrahydro-benzothiazole-6-carbonyl)-pyridin-2-yl]-methyl-carbamic acid tert-butyl ester

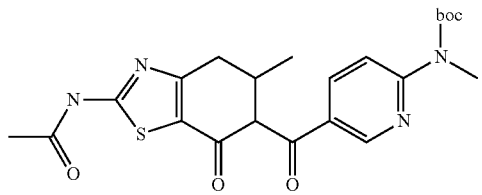

A-13 is prepared via general procedure A1 starting from (5-chlorocarbonyl-pyridin-2-yl)-methyl-carbamic acid tert-butyl ester (A-10) (7.24 g, 26.8 mmol) and N-(5-methyl-7-oxo-4,5,6,7-tetrahydro-benzothiazol-2-yl)-acetamide (A-06) (5.00 g, 22.3 mmol). After evaporation of the solvent 7.72 g of A-13 is obtained that is used without further purification in the next step.

A-14) [5-(2-Acetylamino-5-methyl-7-oxo-4,5,6,7-tetrahydro-benzothiazole-6-carbonyl)-pyridin-2-yl]-ethyl-carbamic acid tert-butyl ester

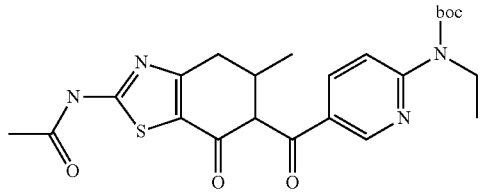

A-14 is prepared via general procedure A1 starting from (5-chlorocarbonyl-pyridin-2-yl)-ethyl-carbamic acid tert-butyl ester (A-09) (7.62 g, 26.8 mmol) and N-(5-methyl-7-oxo-4,5,6,7-tetrahydro-benzothiazol-2-yl)-acetamide (A-06) (5.00 g, 22.3 mmol). After evaporation of the solvent 8.62 g of A-14 are obtained which is used without further purification in the next step.

A-15) N-[5-Methyl-6-(6-methyl-pyridine-3-carbonyl)-7-oxo-4,5,6,7-tetrahydro-benzothiazol-2-yl]acetamide

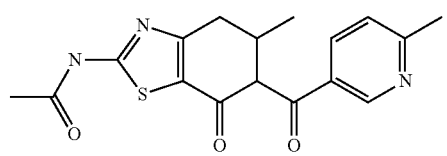 [SMILES: CC(=O)Nc1nc2c(s1)C(=O)C(C(=O)c1ccc(C)nc1)C(C)C2]

A-15 is prepared using general procedure A3 starting from A-06 (1.50 g, 6.67 mmol) and methyl 6-methylnicotinate (1.10 g, 8.02 mmol). The reaction is worked-up with DCM and the product is purified by flash column chromatography (silicagel, 0-12% acetone in ethyl acetate) Yield: 861 mg. HPLC-MS: $t_R$=1.43 min, (M+H)$^+$=344.

A-16) N-[6-(6-Fluoro-pyridine-3-carbonyl)-5-methyl-7-oxo-4,5,6,7-tetrahydro-benzothiazol-2-yl]-acetamide

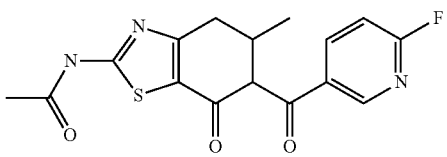 [SMILES: CC(=O)Nc1nc2c(s1)C(=O)C(C(=O)c1ccc(F)nc1)C(C)C2]

A-16 is prepared via general procedure A1 starting from 2-fluoropyridine-5-carbonyl chloride (4.27 g, 26.8 mmol) and N-(5-methyl-7-oxo-4,5,6,7-tetrahydro-benzothiazol-2-yl)-acetamide (A-06) (5.00 g, 22.3 mmol). Yield: 6.20 g. HPLC-MS: $t_R$=0.93 min, (M+H)$^+$=348.

A-17) 2-Amino-6-(6-ethylamino-pyridine-3-carbonyl)-5-methyl-5,6-dihydro-4H-benzothiazol-7-one

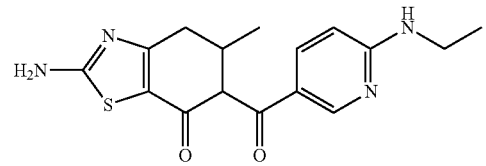 [SMILES: CCNc1ccc(C(=O)C2C(=O)c3sc(N)nc3CC2C)cn1]

To a suspension of 7.70 g (22.2 mmol) of A-16 in THF (50 mL)/isopropanol (50 mL) is added ethylamine (9.09 mL, 112 mmol). The reaction mixture is stirred for 3 d at RT and additional 4 h at 50° C. The solvent is removed under reduced pressure and water and DCM are added to the residue. After phase separation the organic layer is dried over sodium sulfate and the solvent is removed under reduced pressure. The crude product is purified by flash column chromatography (silicagel, 0-20% EtOH in DCM) yielding 6.60 g of A-17 as solid, which is used such as in the next step.

A-18) [6-(6-Ethylamino-pyridine-3-carbonyl)-5-methyl-7-oxo-4,5,6,7-tetrahydro-benzothiazol-2-yl]-carbamic acid methyl ester

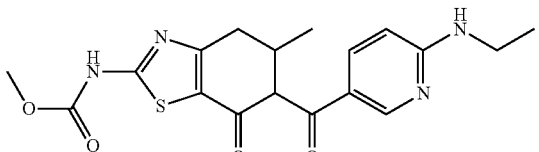

To a suspension of 2.00 g (6.05 mmol) of A-17 and 1,1'-carbonyldiimidazole (2.46 g, 15.1 mmol) in 6 mL acetonitril is added 1,8-diazabicyclo[5.4.0]undec-7-ene (1.8 mL, 12.1 mmol). The reaction mixture is heated in the microwave for 10 min at 90° C. Ammonia in MeOH (951 μL, 7 M, 6.66 mmol) is added and heating is continued for another 10 min at 120° C. Water and DCM are added to the reaction mixture and concentrated HCl (aq.) is added until pH 1 is reached. After phase separation the aqueous layer is extracted five times with DCM and ethylacetate. The combined organic layers are dried over sodium sulfate and the solvent is removed under reduced pressure. Yield: 0.68 g.

HPLC-MS: $t_R$=0.90 min, $(M+H)^+$=389.

A-19) [6-(6-Ethylamino-pyridine-3-carbonyl)-5-methyl-7-oxo-4,5,6,7-tetrahydro-benzothiazol-2-yl]-urea

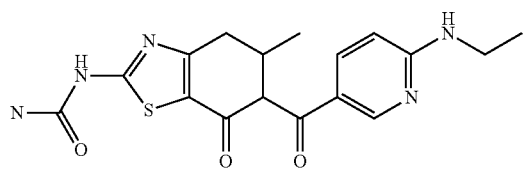 [SMILES: CCNc1ccc(C(=O)C2C(=O)c3sc(NC(N)=O)nc3CC2C)cn1]

To a suspension of 1.00 g (3.03 mmol) of A-17 and 1,1'-carbonyldiimidazole (1.23 g, 7.57 mmol) in 10 mL acetonitril is added 1,8-diazabicyclo[5.4.0]undec-7-ene (905 μL, 6.05 mmol). The reaction mixture is heated in the microwave for 30 min at 120° C. Ammonium chloride (1.13 g, 21.2 mmol) is added and heating is continued for another 10 min at 120° C. Water and DCM are added to the reaction mixture and concentrated HCl (aq.) is added until pH 1 is reached. After phase separation the aqueous layer is washed three times with DCM. The aqueous layer is evaporated under reduced pressure. The resultant crude mixture is used without further purification for the next step.

A-20) 1-[6-(6-Ethylamino-pyridine-3-carbonyl)-5-methyl-7-oxo-4,5,6,7-tetrahydro-benzothiazol-2-yl]-3-methyl-urea

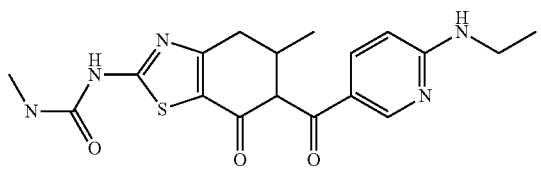 [SMILES: CCNc1ccc(C(=O)C2C(=O)c3sc(NC(=O)NC)nc3CC2C)cn1]

To a suspension of 1.00 g (3.03 mmol) of A-17 and 1,1'-carbonyldiimidazole (1.20 g, 7.40 mmol) in 3 mL acetonitril is added 1,8-diazabicyclo[5.4.0]undec-7-ene (696 μL, 4.54 mmol). The reaction mixture is heated in the microwave for 10 min at 90° C. Methylamine in THF (3.33 mL, 6.65 mmol) is added and heating is continued for another 10 min at 120° C. Water and DCM are added to the reaction mixture and concentrated HCl (aq.) is added until pH 1 is reached. After phase separation the aqueous layer is washed three times with DCM. The aqueous layer is evaporated under reduced pressure. The resultant crude mixture is taken up in DMSO/water and purified by reverse phase chromatography. Yield: 342 mg. HPLC-MS: $t_R$=0.90 min, $(M+H)^+$=388.

A-21) N-[6-(6-Fluoro-pyridine-3-carbonyl)-5,5-dimethyl-7-oxo-4,5,6,7-tetrahydro-benzothiazol-2-yl]-acetamide

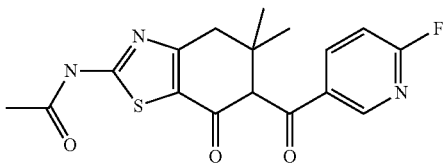 [SMILES: CC(=O)Nc1nc2c(s1)C(=O)C(C(=O)c1ccc(F)nc1)C(C)(C)C2]

A-21 is prepared via general procedure A1 starting from 2-fluoro pyridine-5-carbonyl chloride (1.00 g, 6.29 mmol) and A-03 (1.00 g, 4.20 mmol). Yield: 1.30 g. which is used as such in the next step.

A-22) N-[6-(6-Amino-pyridine-3-carbonyl)-5,5-dimethyl-7-oxo-4,5,6,7-tetrahydro-benzothiazol-2-yl]-acetamide

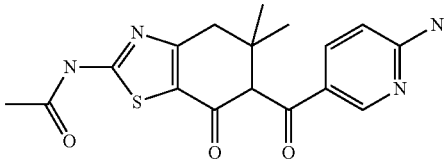 [SMILES: CC(=O)Nc1nc2c(s1)C(=O)C(C(=O)c1ccc(N)nc1)C(C)(C)C2]

To a solution of 2.00 g (5.53 mmol) of A-21 in THF (20 mL)/isopropanol (20 mL) is added an ammonia solution (27.6 mL, 32% in water, 221 mmol). The reaction mixture is stirred for 3 days at RT. The solvent is removed under reduced pressure, water is added and the mixture is extracted three times with ethylacetate. The combined organic layers are washed with brine, dried over $MgSO_4$ and the solvent is removed under reduced pressure. The crude product is taken up is purified by reverse phase chromatography yielding 630 mg of the desired product as a crude which is used as such in the next step.

A-23) 1,1-Dimethyl-3-(5-spirocyclopropyl-7-oxo-4,5,6,7-tetrahydro-benzothiazol-2-yl)-urea

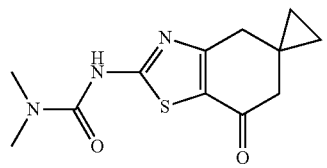 [SMILES: CN(C)C(=O)Nc1nc2c(s1)C(=O)CC1(CC1)C2]

To a suspension of 1.05 (5.41 mmol) of A-07 and 1,1'-carbonyldiimidazole (1.75 g, 10.8 mmol) in 30 mL acetonitril is added 1,8-diazabicyclo[5.4.0]undec-7-ene (1.62 mL, 10.8 mmol). The reaction mixture is stirred at 88° C. over night. The reaction mixture is cooled down and dimethylamine in THF (18.9 mL, 2 M solution, 37.8 mmol) is added and heating is continued for 20 min at 120° C. in the microwave. The solvent is removed under reduced pressure, water is added and pH is adjusted to 3-4 with 5 N HCl (aq.). The solution is extracted three times with ethylacetate. The combined organic layers are washed with brine, dried over MgSO$_4$ and the solvent is removed under reduced pressure yielding 1.2 g of the desired product as a crude which is used as such in the next step.

A-24) 3-[5-Spirocyclopropyl-6-(6-fluoro-pyridine-3-carbonyl)-7-oxo-4,5,6,7-tetrahydro-benzothiazol-2-yl]-1,1-dimethyl-urea

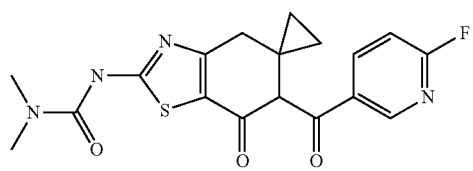 [SMILES: CN(C)C(=O)Nc1nc2c(s1)C(=O)C(C(=O)c1ccc(F)nc1)C1(CC1)C2]

A-24 is prepared via general procedure A1 starting from 2-fluoro pyridine-5-carbonyl chloride (1.44 g, 9.05 mmol) and A-23 (1.20 g, 4.52 mmol). Yield: 2.00 g (crude) which is used as such in the next step.

A-25) 3-[5-Spirocyclopropyl-6-(6-ethylamino-pyridine-3-carbonyl)-7-oxo-4,5,6,7-tetrahydro-benzothiazol-2-yl]-1,1-dimethyl-urea

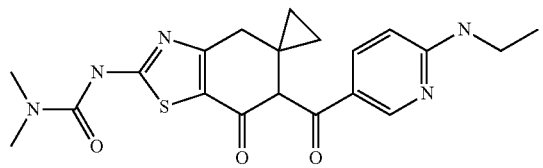 [SMILES: CCNc1ccc(C(=O)C2C(=O)c3sc(NC(=O)N(C)C)nc3CC23CC3)cn1]

To a solution of 1.00 g (1.54 mmol) of A-24 in THF (9 mL)/isopropanol (9 mL) is added ethylamine in THF (5.79 mL, 2 M sol., 11.6 mmol). The reaction mixture is stirred for 3 days at RT. The solvent is removed under reduced pressure, water is added and the mixture is extracted three times with ethylacetate. The combined organic layers are washed with brine, dried over MgSO$_4$ and the solvent is removed under reduced pressure. The crude product is used as such in the next step.

A-26) (2-Acetylamino-5-methyl-7-oxo-4,5,6,7-tetrahydro-benzothiazol-6-yl)-oxo-acetic acid methyl ester

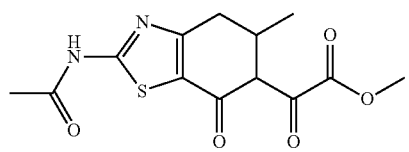 [SMILES: COC(=O)C(=O)C1C(=O)c2sc(NC(C)=O)nc2CC1C]

To a stirred solution of A-06 (4.72 g, 20.0 mmol) in 75 ml DMF is added sodium methylate (4.32 g, 80.0 mmol) under nitrogen at RT. Dimethyloxalate (4.77 g, 40.0 mmol) is added and stirring is continued for 3 h. The reaction mixture is cooled to 0° C., 100 mL water and 6.63 mL concentrated HCl (aq.) are added carefully. The pH of the mixture is adjusted to pH 5 by the addition of potassium carbonate. Insoluble material is filtered off, washed with water taken up in water/acetonitril (v/v, 9/1) and freeze dried. Yield 3.00 g. (M−H)$^-$=309.

A-27) 7-Acetylamino-1-isopropyl-4-methyl-4,5-dihydro-1H-pyrazolo[4,3-g]benzothiazole-3-carboxylic acid

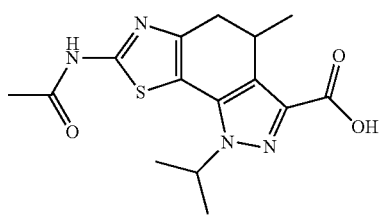 [SMILES: CC(=O)Nc1nc2c(s1)-c1c(c(C(=O)O)nn1C(C)C)C(C)C2]

A mixture of B-34 (2.54 g, 7.29 mmol) and lithium hydroxide mono hydrate (776 mg, 18.2 mmol) in 30 mL dioxane and 30 mL water is stirred at 50° C. for 3 h. 1 M aqueous HCl solution is added to the reaction mixture until pH 4 is reached. While the reaction mixture is allowed to cool down a precipitation is formed. 50 mL water is added and most of the dioxane is evaporated under reduced pressure. The residue is filtered, washed twice with water (20 mL each) and freeze dried. Yield: 1.68 g. HPLC-MS: R$_t$=0.41 min, (M+H)$^+$=335.

Examples B

Examples B-01 to B-34 are synthesized according to the following general procedure. The appropriate hydrazine and diketone required for synthesis can be deduced from the table of examples.

General Procedure B:

The appropriate diketone (1 eq.) and the appropriate hydrazine or hydrazine salt (1-10 eq.) are added to acetic acid and heated to 60° C.-90° C. for 1-16 h. The acetic acid is removed under reduced pressure and the residue is taken up in water. The reaction mixture is neutralized to pH 5-6 with aqueous 10N NaOH and extracted with DCM. The combined organic phases are washed with water and brine, dried on MgSO$_4$ and the solvents are removed under reduced pressure. The product may be purified by NP or RP column chromatography.

TABLE 1

Examples B1-B34

| No. | MOLSTRUCTURE | Diketone | Hydrazine | $t_R$ (min.) | $(M + H)^+$ |
|---|---|---|---|---|---|
| B1 | | A-15 | cyclopentyl hydrazine | 2.1 | 408 |
| B2 | | A-15 | isopropyl hydrazine | 1.88 | 382 |
| B3 | | A-15 | o-tolyl hydrazine | 1.93 | 430 |
| B4 | | A-15 | (1-cyclopropyl-piperidin-4-yl)-hydrazine | 1.92 | 463 |
| B5 | | A-18 | tert-butyl hydrazine | 1.71 | 441 |

TABLE 1-continued

Examples B1-B34

| No. | MOLSTRUCTURE | Diketone | Hydrazine | $t_R$ (min.) | $(M + H)^+$ |
|---|---|---|---|---|---|
| B6 | | A-18 | isopropyl hydrazine | 1.49 | 427 |
| B7 | | A-18 | o-tolyl hydrazine | 1.61 | 475 |
| B8 | | A-18 | 2-fluoro-phenyl hydrazine | 1.53 | 479 |
| B9 | | A-20 | isopropyl hydrazine | 1.63 | 426 |
| B10 | | A-20 | o-tolyl hydrazine | 1.71 | 474 |

TABLE 1-continued

Examples B1-B34

| No. | MOLSTRUCTURE | Diketone | Hydrazine | $t_R$ (min.) | $(M + H)^+$ |
|---|---|---|---|---|---|
| B11 | | A-19 | isopropyl hydrazine | 1.57 | 410 [M − H] |
| B12 | | A-19 | o-tolyl hydrazine | 1.65 | 460 |
| B13 | | A-17 | o-tolyl hydrazine | 0.87 | 417 |
| B14 | | A-14 | o-tolyl hydrazine | 1.67 | 459 |
| B15 | | A-14 | isopropyl hydrazine | 1.59 | 411 |
| B16 | | A-14 | benzyl hydrazine | 1.72 | 459 |

TABLE 1-continued

Examples B1-B34

| No. | MOLSTRUCTURE | Diketone | Hydrazine | $t_R$ (min.) | $(M + H)^+$ |
|---|---|---|---|---|---|
| B17 | | A-14 | pyridine-3yl-methyl hydrazine | 1.41 | 460 |
| B18 | | A-14 | sec-butyl hydrazine | 1.49 | 425 |
| B19 | | A-14 | (2,2,2)-trifluoroethyl hydrazine | 1.45 | 451 |
| B20 | | A-14 | t-butyl hydrazine | 1.31 | 369 |
| B21 | | A-13 | isopropyl hydrazine | 1.56 | 397 |

TABLE 1-continued

Examples B1-B34

| No. | MOLSTRUCTURE | Diketone | Hydrazine | $t_R$ (min.) | $(M + H)^+$ |
|---|---|---|---|---|---|
| B22 | | A-13 | o-tolyl hydrazine | 1.62 | 445 |
| B23 | | A-13 | benzyl hydrazine | 1.62 | 445 |
| B24 | | A-13 | pyridine-3yl-methyl hydrazine | 1.31 | 446 |
| B25 | | A-13 | sec-butyl hydrazine | 1.63 | 411 |
| B26 | | A-13 | (tetrahydro-thiopyran-4-yl)-hydrazine | 1.61 | 455 |

TABLE 1-continued

Examples B1-B34

| No. | MOLSTRUCTURE | Diketone | Hydrazine | $t_R$ (min.) | $(M + H)^+$ |
|---|---|---|---|---|---|
| B27 | | A-13 | (2,2,2)-trifluoroethyl hydrazine | 1.47 | 437 |
| B28 | | A-15 | 3-hydrazino-propionitrile | 0.90 | 393 |
| B29 | | A-15 | 2-fluoro-phenyl hydrazine | 1.36 | 434 |
| B30 | | A-15 | 2-hydrazino-ethanol | 1.07 | 384 |
| B31 | | A-22 | o-tolyl hydrazine | 1.42 | 445 |

TABLE 1-continued

Examples B1-B34

| No. | MOLSTRUCTURE | Diketone | Hydrazine | $t_R$ (min.) | $(M + H)^+$ |
|---|---|---|---|---|---|
| B32 | | A-22 | isopropyl hydrazine | 1.32 | 397 |
| B33 | | A-25 | o-tolyl hydrazine | 1.75 | 500 |
| B34 | | A-26 | isopropyl hydrazine | 1.32 | 349 |

Examples C

Examples C-01 to C-23 are synthesized from example A-27 according to the following general procedure. The appropriate amine required for synthesis can be deduced from the table of examples.

General Procedure C:

The example A-27 (1 eq.) is taken up in DMA, DIPEA (2.5 eq.) and HATU (1.3 eq.) are added and the reaction mixture is stirred for 10 min at RT. Amine is added and the reaction mixture is stirred overnight at RT followed by 1 h at 55° C. The product is purified by HPLC (C18, 5-98% acetonitrile in water containing 0.1% formic acid).

TABLE 2

Examples C1-C23

| No. | MOLSTRUCTURE | Amine | $t_R$ (min.) | $(M + H)^+$ |
|---|---|---|---|---|
| C1 | | N,N,N'-trimethyl-ethane-1,2-diamine | 1.38 | 419 |

TABLE 2-continued

Examples C1-C23

| No. | MOLSTRUCTURE | Amine | $t_R$ (min.) | $(M + H)^+$ |
|---|---|---|---|---|
| C2 | | benzyl-methyl-amine | 1.78 | 438 |
| C3 | | 3-amino-propionic acid methyl ester | 1.49 | 420 |
| C4 | | 4-amino-butyric acid ethyl ester | 1.63 | |
| C5 | | benzyl-amine | 1.78 | 424 |
| C6 | | (2-methoxy-ethyl)-methyl-amine | 1.39 | 406 |

TABLE 2-continued

Examples C1-C23

| No. | MOLSTRUCTURE | Amine | $t_R$ (min.) | $(M + H)^+$ |
|---|---|---|---|---|
| C7 | | (3-methoxy-propyl)-methyl-amine | 1.50 | 406 |
| C8 | | (2-methoxy-ethyl)-amine | 1.43 | 392 |
| C9 | | ammonia | 1.21 | 334 |
| C10 | | N,N,N'-trimethyl-propane-1,3-diamine | 1.45 | 433 |
| C11 | | 2H-pyrazol-3-ylamine | 1.38 | 400 |

TABLE 2-continued

Examples C1-C23

| No. | MOLSTRUCTURE | Amine | $t_R$ (min.) | $(M + H)^+$ |
|-----|--------------|-------|--------------|-------------|
| C12 | | 2-amino-N,N-dimethyl-acetamide | 1.34 | 419 |
| C13 | | dimethylamine | 1.33 | 362 |
| C14 | | $N^1,N^1$-dimethyl-ethane-1,2-diamine | 1.42 | 405 |
| C15 | | methylamine | 1.50 | 348 |
| C16 | | 2-amino-ethanol | 1.21 | 378 |

TABLE 2-continued

Examples C1-C23

| No. | MOLSTRUCTURE | Amine | $t_R$ (min.) | $(M + H)^+$ |
| --- | --- | --- | --- | --- |
| C17 | | 3-amino-propanol | 1.27 | 392 |
| C18 | | N-methyl aniline | 1.65 | 424 |
| C19 | | 2-methylamino-ethanol | 1.18 | 392 |
| C20 | | aniline | 1.80 | 410 |
| C21 | | 3-methylamino-propanol | 1.23 | 406 |

TABLE 2-continued

Examples C1-C23

| No. | MOLSTRUCTURE | Amine | $t_R$ (min.) | $(M + H)^+$ |
|---|---|---|---|---|
| C22 | 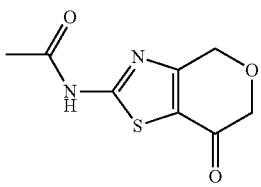 | $N^1,N^1$-dimethyl-propane-1,3-diamine | 1.52 | 419 |
| C23 | 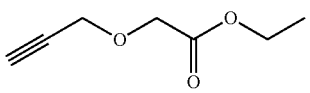 | N,N-dimethyl-2-methylamino-acetamide | 1.29 | 433 |

Intermediates D

D-01) N-(7-Oxo-6,7-dihydro-4H-pyrano[3,4-d]thiazol-2-yl)-acetamide

D-01A) Prop-2-ynyloxy-acetic acid ethyl ester

A solution of prop-2-yn-1-ol (815 g, 14.5 mol) in THF (1 L) is added dropwise to a suspension of NaH (60% content) (500 g) in THF (4 L) at 0° C. under nitrogen atmosphere. The stirring is continued at this temperature for 3 h before a solution of bromo-acetic acid ethylester (2.17 kg, 13.0 mol) in THF (2 L) is added dropwise over 1 h. After addition, the temperature is allowed to warm to RT and the reaction mixture is stirred for another 3 h. HCl (2 M, 8 L) is added into the reaction mixture, the organic layer is isolated and the aqueous layer is extracted with EtOAc (3×5 L). The combined organic layer is washed with brine (2 L), dried over anhydrous $Na_2SO_4$ and concentrated in vacuo. The crude oil is distilled to give the desired product. Yield: 1.6 kg. $^1$H NMR: (CDCl$_3$) δ 4.31 (s, 2H), 4.23 (q, J=7.2 Hz, 2H), 4.19 (s, 2H), 2.47 (t, J=2.4 Hz, 1H), 1.29 (t, J=7.2 Hz, 3H).

D-01B) (2-Oxo-propoxy)-acetic acid methyl ester

Hg(OAc)$_2$ (385 g, 1.1 mol) is added into a solution of D-01A (1.56 kg, 11.0 mol) in MeOH (10 L) in portions and next conc. $H_2SO_4$ (55 mL) is added dropwise. The mixture is refluxed for 1 h. After cooling to RT, the reaction mixture is concentrated in vacuo to a volume of 4 L. HCl (1M, 4.25 L) is added and the aqueous layer is extracted with DCM (5×3 L). The combined organic layer is dried over anhydrous $Na_2SO_4$ and concentrated in vacuo to give a crude product (1.8 kg) which is distilled in vacuo to give the title compound. Yield: 1.2 kg.

D-01C) 5-Hydroxy-6H-pyran-3-one

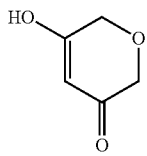

A solution of D-01B (1.04 kg, 6.5 mol) in anhydrous Et$_2$O (20 L) is added dropwise over 2 h to a solution of t-BuOK (680 g, 6.07 mol) in t-BuOH (7 L) and Et$_2$O (10 L) at rt. After stirring for 2 h, HCl (2M, 4 L) is added. The layers are separated and the aqueous layer is extracted with EtOAc (2×10 L). The combined organic layer is washed with brine (2×4 L), dried over anhydrous Na$_2$SO$_4$ and concentrated in vacuo (below 35° C.) to give crude oil (600 g). The crude product is recrystallized from EtOAc/petroleum ether (1:1) to afford the desired product. Yield: 152 g. $^1$H NMR: (DMSO-d$_6$) δ 11.80 (brs, 1H), 5.30 (s, 1H), 4.12-3.87 (s, 4H).

D-01D) 2-Amino-4H-pyrano[3,4-d]thiazol-7-one

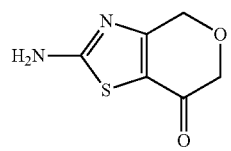

D-01C (75.0 g 0.658 mol) and NaOAc (81.0 g 0.988 mol) are suspended in AcOH (750 mL). Br$_2$ (105.0 g 0.656 mol) is added dropwise while maintaining the reaction temperature between 15 to 20° C. The reaction is then allowed to stir at RT for 2 h. Thiourea (50.0 g 0.658 mol) is added and the mixture heated at 100° C. overnight. The AcOH is removed in vacco and the residue is washed with water and hot EtOAc. After drying in vacuo, the desired product is obtained as a gray powder. Yield: 50 g. $^1$H NMR: (DMSO-d$_6$) δ 8.43 (brs, 2H) 4.64 (s, 2H) 4.11 (s, 2H).

Compound D-01D (50.0 g, 0.294 mol) is added to Ac$_2$O (700 mL) and the mixture is heated at 100° C. for 5 h. The reaction solution is cooled to RT and the produced solid is collected by filtration, washed with AcOH, EtOAc and water to afford the desired product as a brown solid. Yield: 46.5 g. $^1$H NMR: (DMSO-d$_6$) δ 12.76 (br s, 1H), 4.82 (s, 2H), 4.21 (s, 2H), 2.18 (s, 3H).

D-02) 1,1-Dimethyl-3-(7-oxo-6,7-dihydro-4H-pyrano[3,4-d]thiazol-2-yl)-urea

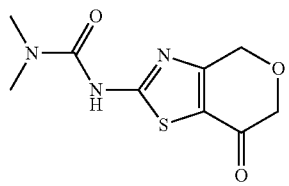 [SMILES: CN(C)C(=O)Nc1nc2c(s1)C(=O)COC2]

To a suspension of D-01D (8.0 g, 47 mmol) in 45 mL acetonitrile is added N,N'-carbonyl-di-imidazole (13.7 g, 84.6 mmol) and 1,8-DBU (6.33 g, 42.3 mmol). The reaction mixture is stirred over night at 100° C. 2 M dimethylamine solution in THF (47.0 mL, 94 mmol) is added and stirring is continued over night at 100° C. The reaction mixture is evaporated and the residue is poured into ice-water. The pH of the mixture is adjusted to pH 5 with 6 M HCl solution. The aqueous mixture is extracted twice with ethylacetate (150 mL each). The combined organic layers are dried over MgSO$_4$ and evaporated under reduced pressure. The crude product is purified via column chromatography (silica, 0-20% EtOH in DCM). Yield: 3.7 g. (M+H)$^+$: 242.

D-03) N-(7-oxo-6,7-dihydro-4H-thiopyrano[3,4-d]thiazol-2-yl)-acetamide

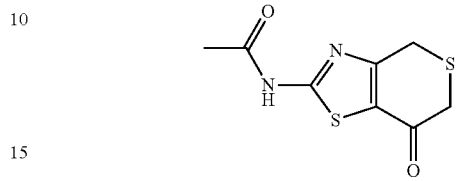

D-03A) (2-Oxo-propylsulfanyl)-acetic acid methyl ester

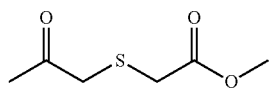

To a mixture of a 5.4 M methanolic solution of sodium methylate (185 mL, 1.00 mol) in 500 mL methanol is added mercapto-acetic acid methyl ester (97.0 g, 912 mmol) at RT. After stirring for 20 minutes at RT chloro acetone (80 mL, 1.0 mmol) is added carefully. After complete addition the reaction mixture is heated at reflux for 20 minutes. The reaction mixture is added to water and extracted with diethyl ether. The organic layer is washed with brine, dried over Na$_2$SO$_4$ and the solvent is evaporated under reduced pressure. The crude reaction product is distilled under reduced pressure (75° C.-90° C., 0.3 mbar) yielding the desired product as colorless liquid. Yield: 61.5 g. (M+H)$^+$=163

D-03B) 5-Hydroxy-6H-thiopyran-3-one

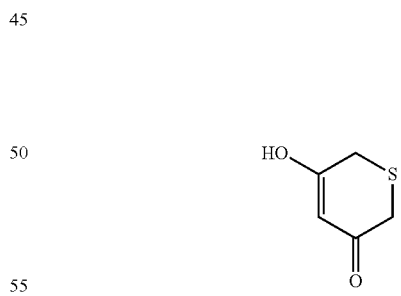

To sodium hydride (13.6 g, 340 mmol) in 800 mL THF at −10° C. is added dropwise D-03A (50.0 g, 308 mmol) in 1 L THF. After complete addition the reaction mixture is allowed to come to RT and stirring is continued for 3 hours. The formed precipitation is filtered off and dissolved in 200 mL water. The aqueous solution is extracted with diethyl ether, acidified with 2 N HCl solution (pH 2) and extracted five times with CHCl$_3$ (200 mL each). The combined CHCl$_3$ phases are washed with brine, dried over Na$_2$SO$_4$ and the solvent is evaporated under reduced pressure. The product is recrystallized from diethylether yielding the desired product as pale yellow solid. Yield: 15 g.

D-03C) 4-Bromo-5-hydroxy-6H-thiopyran-3-one

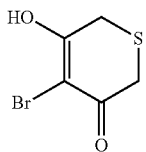

To a suspension of D-03B (39.0 g, 300 mmol) in 80 mL water is added dropwise $Br_2$ (15.4 mL, 300 mol). The reaction mixture is stirred for 1 hour at RT. The precipitate is filtered off. The residue is triturated with water, washed with diethyl ether, dried under reduced pressure and used as such in the next step. Yield: 45.2 g.

D-03D) 2-Amino-4H-thiopyrano[3,4-d]thiazol-7-one

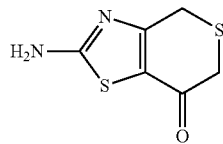 [SMILES: Nc1nc2c(s1)C(=O)CSC2]

A reaction mixture of D-03C (45.2 g, 216 mmol) and thiourea (18.0 g, 237 mmol) in 400 mL ethanol is stirred under reflux for 4 hours. The reaction mixture is diluted with methanol and the insoluble material is filtered off. The residue is taken up in DMSO and added to water. The formed precipitate is filtered off, washed with methanol and diethyl ether and dried in vacuo. Yield: 27.1 g. $(M+H)^+=187$.

A suspension of D-03D in acetic anhydride is refluxed for 6 hours. After cooling to RT diethyl ether is added, the insoluble material is filtered off and washed with water. The crude product is taken up in DMSO and added dropwise to water. The precipitate is filtered off, washed with methanol and water and dried in vacuo. Yield: 29.2 g. $(M+H)^+=229$.

D-04) N-[7-Oxo-6-(2,2,2-trifluoro-acetyl)-6,7-dihydro-4H-pyrano[3,4-d]thiazol-2-yl]-acetamide

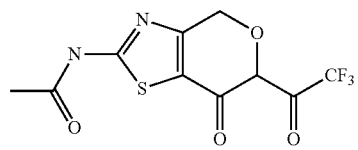 [SMILES: CC(=O)Nc1nc2c(s1)C(=O)C(C(=O)C(F)(F)F)OC2]

D-04 is prepared using general procedure A3 starting from D-01 (1.00 g, 4.71 mmol) and trifluoroacetyl imidazole (1.20 mL, 10.5 mmol, Aldrich). The reaction is worked-up with DCM and the product is purified by flash column chromatography (silica gel, 0-20% EtOH in DCM). Yield: 223 mg. HPLC: $t_R=2.98$ min.

D-05) N-(6-Cyclopropanecarbonyl-7-oxo-6,7-dihydro-4H-pyrano[3,4-d]thiazol-2-yl)-acetamide

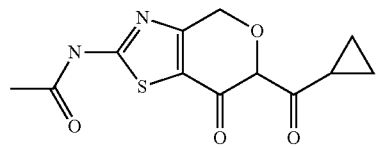 [SMILES: CC(=O)Nc1nc2c(s1)C(=O)C(C(=O)C1CC1)OC2]

D-05 is prepared using general procedure A2 starting from D-01 (1.00 g, 4.71 mmol) and cyclopropanecarboxylic acid ethyl ester (2.30 mL, 19.0 mmol). The reaction is worked-up by adding 1.8 mL acetic acid and 40 mL aqueous NaCl solution (half saturated) to the reaction mixture. After cooling to 0° C. and stirring the precipitated product is filtered off, washed with water and dried. Yield: 993 mg. HPLC-MS: $t_R=1.08/1.30$ min (Keto-Enol), $(M+H)^+=281$.

D-06) N-[7-Oxo-6-(pyridine-3-carbonyl)-6,7-dihydro-4H-pyrano[3,4-d]thiazol-2-yl]-acetamide

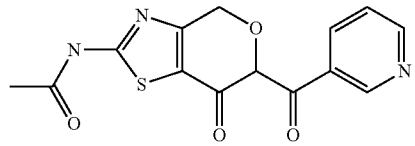 [SMILES: CC(=O)Nc1nc2c(s1)C(=O)C(C(=O)c1cccnc1)OC2]

D-06 is prepared using general procedure A3 starting from D-01 (1.15 g, 5.42 mmol) and nicotinic acid (1.33 g, 10.8 mmol). The reaction is worked-up with DCM and the product is purified by flash column chromatography (silica gel, 0-20% EtOH in DCM). The desired product was used without further purification in the next step.

D-07) N-[6-(6-Methoxy-pyridine-3-carbonyl)-7-oxo-6,7-dihydro-4H-pyrano[3,4-d]thiazol-2-yl]-acetamide

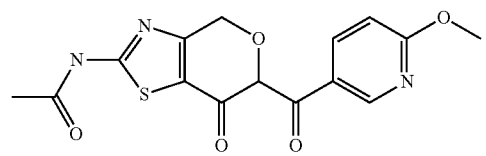 [SMILES: COc1ccc(C(=O)C2OCc3nc(NC(C)=O)sc3C2=O)cn1]

D-07 is prepared using general procedure A2 starting from D-01 (3.00 g, 14.1 mmol) and methyl 6-methoxynicotinate (3.70 g, 21.7 mmol). The product is used in the next step without further purification. Yield: 3.70 g. HPLC-MS: $t_R$=1.34 min, (M+H)$^+$=348.

D-08) N-(6-Formyl-7-oxo-6,7-dihydro-4H-pyrano[3,4-d]thiazol-2-yl)-acetamide

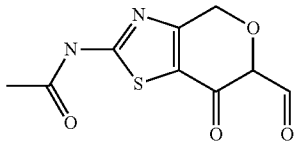 [SMILES: CC(=O)Nc1nc2c(s1)C(=O)C(C=O)OC2]

D-08 is prepared using general procedure A2 starting from D-01 (1.18 g, 5.56 mmol) and formic acid ethyl ester (9.44 g, 111 mmol). The product is used in the next step without further purification. Yield: 863 mg.

D-09) N-[6-(6-Fluoro-pyridine-3-carbonyl)-7-oxo-6,7-dihydro-4H-pyrano[3,4-d]thiazol-2-yl]-acetamide

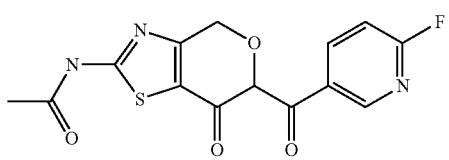 [SMILES: CC(=O)Nc1nc2c(s1)C(=O)C(C(=O)c1ccc(F)nc1)OC2]

D-09 is prepared via general procedure A1 starting from D-01 (1.00 g, 4.71 mmol) and 2-fluoropyridine-5-carbonyl chloride (958 mg, 6.00 mmol). The crude product is used in the next step without further purification. Yield: 1.18 g.

D-10) [5-(2-Acetylamino-7-oxo-6,7-dihydro-4H-pyrano[3,4-d]thiazole-6-carbonyl)-pyridin-2-yl] ethyl-carbamic acid tert-butyl ester

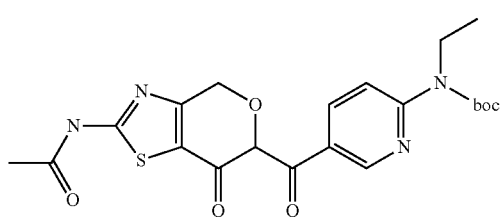

D-10 is prepared via general procedure A1 starting from D-01 (265 mg, 1.24 mmol) and (5-chlorocarbonyl-pyridin-2-yl)-ethyl-carbamic acid tert-butyl ester (A-09) (500 mg, 1.75 mmol). The product is used in the next step without further purification.

Yield: 600 mg.

D-11) [5-(2-Acetylamino-7-oxo-6,7-dihydro-4H-pyrano[3,4-d]thiazole-6-carbonyl)-pyridin-2-yl]-methyl-carbamic acid tert-butyl ester

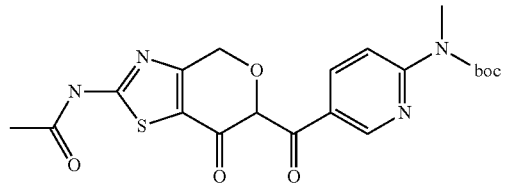

D-11 is prepared via general procedure A1 starting from D-01 (6.55 g, 30.9 mmol) and (5-chlorocarbonyl-pyridin-2-yl)-methyl-carbamic acid tert-butyl ester (A-10) (10.7 g, 39.5 mmol). The product is purified by flash column chromatography (silica gel, 0-80% ethyl acetate in cyclohexane). Yield: 2.0 g.

D-12) {5-[2-(3,3-Dimethyl-ureido)-7-oxo-6,7-dihydro-4H-pyrano[3,4-d]thiazole-6-carbonyl]-pyridin-2-yl}-ethyl-carbamic acid tert-butyl ester

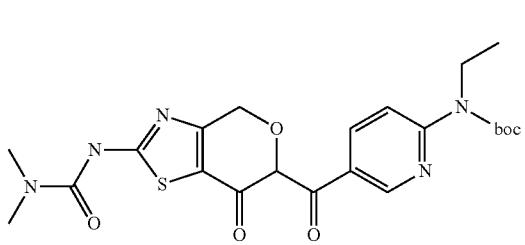

D-12 is prepared via general procedure A1 starting from D-02 (1.71 g, 7.11 mmol) and (5-chlorocarbonyl-pyridin-2-yl)-ethyl-carbamic acid tert-butyl ester (A-09) (1.35 g, 4.74 mmol). The crude product is used without further purification in the next step.

Yield: 1.3 g.

D-13) N-[7-Oxo-6-(pyridine-3-carbonyl)-6,7-dihydro-4H-thiopyrano[3,4-d]thiazol-2-yl]-acetamide

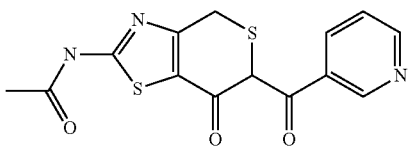 [SMILES: CC(=O)Nc1nc2c(s1)C(=O)C(C(=O)c1cccnc1)SC2]

D-13 is prepared using general procedure A3 starting from D-03 (200 mg, 0.87 mmol) and nicotinic acid (160 mg, 1.31 mmol). The crude product is used without further purification in the next step. Yield: 180 mg.

D-14) N-[6-(6-Methyl-pyridine-3-carbonyl)-7-oxo-6,7-dihydro-4H-thiopyrano[3,4-d]thiazol-2-yl]-acetamide

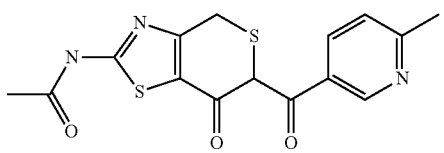 [SMILES: CC(=O)Nc1nc2c(s1)C(=O)C(C(=O)c1ccc(C)nc1)SC2]

D-14 is prepared using general procedure A3 starting from D-03 (1.00 g, 4.38 mmol) and 6-methyl nicotinic acid (900 mg, 6.57 mmol). The product is purified by flash column chromatography (silica gel, 0-20% MeOH in DCM). Yield: 1.1 g.

D-15) N-(6-Formyl-7-oxo-6,7-dihydro-4H-thiopyrano[3,4-d]thiazol-2-yl)-acetamide

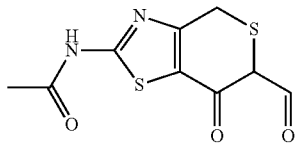 [SMILES: CC(=O)Nc1nc2c(s1)C(=O)C(C=O)SC2]

To a solution of D-03 (10.0 g, 77 mmol) in 50 mL DMSO is added sodium tert-pentoxide (14.4 g, 131 mmol). The reaction mixture is stirred for 30 min at RT, cooled to 10° C. and a solution of ethyl formate (5.3 mL, 66 mmol) in 20 mL DMSO is added dropwise. After complete addition the reaction mixture is stirred for 6 hours at RT. The reaction mixture is poured into 200 mL cold water. Acetic acid is added at 10° C.-15° C. until pH 5 is reached. The mixture is extracted with ethyl acetate. The combined ethyl acetate layers are washed with brine and dried over $Na_2SO_4$. After evaporation of the solvent under reduced pressure the desired product is obtained, which is used without further purification in the next step.
Yield: 5.8 g.

D-16) (7-Oxo-6,7-dihydro-4H-thiopyrano[3,4-d]thiazol-2-yl)-carbamic acid methyl ester

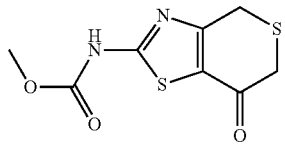

To a suspension of D-03d (34.1 g, 183 mmol) in 2.5 L THF sodium tert-pentoxide (30.2 g, 275 mmol) is added at RT. Afterwards methyl chloroformate (21.1 mL, 275 mmol) is added at 50° C. and stirring is continued for 3 hours at reflux. The reaction mixture is evaporated and taken up in ethyl acetate and brine. The organic layer is dried over $Na_2SO_4$ and the solvent is evaporated under reduced pressure to give the desired product.
Yield: 25.2. $(M+H)^+$: 245.

D-17) (6-Formyl-7-oxo-6,7-dihydro-4H-thiopyrano[3,4-d]thiazol-2-yl)-carbamic acid methyl ester

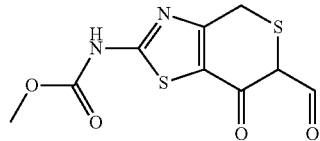 [SMILES: COC(=O)Nc1nc2c(s1)C(=O)C(C=O)SC2]

To a solution of D-16 (9.5 g, 38.9 mmol) in 50 mL DMSO is added sodium tert-pentoxide (12.9 g, 117 mmol). The reaction mixture is stirred for 30 min at RT, cooled to 10° C. and a solution of ethyl formate (3.6 mL, 58 mmol) in 20 mL DMSO is added dropwise. After complete addition the reaction mixture is stirred for 6 hours at RT. The reaction mixture is poured into 200 mL cold water. Acetic acid is added at 10° C.-15° C. until pH 5 is reached. The mixture is extracted with ethyl acetate. The combined ethyl acetate layers are washed with brine and dried over $Na_2SO_4$. After evaporation of the solvent under reduced pressure the desired product is obtained which is used without further purification in the next step.
Yield: 5.3 g.

Examples E

Examples E-01 to E-42 are synthesized according to general procedure B. The appropriate hydrazine and diketone required for synthesis can be deduced from the table of examples.

TABLE 3

Examples E01-E42

| No. | MOLSTRUCTURE | Diketone | Hydrazine | $t_R$ (min.) | $(M + H)^+$ |
|---|---|---|---|---|---|
| E-01 | (structure) | D-04 | 2-chloro phenyl hydrazine | 3.24 | 415/417 |

TABLE 3-continued

Examples E01-E42

| No. | MOLSTRUCTURE | Diketone | Hydrazine | $t_R$ (min.) | $(M + H)^+$ |
|---|---|---|---|---|---|
| E-02 | | D-04 | 2-bromo-phenyl hydrazine | 3.24 | 459/461 |
| E-03 | | D-04 | 2-trifluormethyl phenyl hydrazine | 3.25 | 449 |
| E-04 | | D-04 | phenyl hydrazine | | 381 |
| E-05 | | D-06 | 2-chloro phenyl hydrazine | | |
| E-06 | | D-08 | methyl hydrazine | 0 | 251 |

TABLE 3-continued

Examples E01-E42

| No. | MOLSTRUCTURE | Diketone | Hydrazine | $t_R$ (min.) | $(M + H)^+$ |
|---|---|---|---|---|---|
| E-07 | | D-09 | 2-bromo phenyl hydrazine | 1.46 | 486/488 |
| E-08 | | D-10 | 2-bromo phenyl hydrazine | 1.46 | 511/513 |
| E-09 | | D-10 | isopropyl hydrazine | 1.43 | 399 |
| E-10 | | D-12 | isopropyl hydrazine | | 428 |
| E-11 | | D-12 | 2-bromo phenyl hydrazine | 1.49 | 540/542 |
| E-12 | | D-11 | isopropyl hydrazine | 1.42 | 385 |

TABLE 3-continued

Examples E01-E42

| No. | MOLSTRUCTURE | Diketone | Hydrazine | $t_R$ (min.) | $(M + H)^+$ |
|---|---|---|---|---|---|
| E-13 | | D-13 | (4-hydrazino-benzyl)-dimethyl-amine | | 463 |
| E-14 | | D-13 | 3-chloro-4-hydrazino-N,N-dimethyl-benzamide | 1.63 | 511 |
| E-15 | | D-06 | 3-chloro-4-hydrazino-benzoic acid methyl ester | 2.45 | 482/484 |
| E-16 | | D-14 | 4-hydrazino-benzaldehyde O-methyl-oxime | 2.08 | 477 |

TABLE 3-continued

Examples E01-E42

| No. | MOLSTRUCTURE | Diketone | Hydrazine | $t_R$ (min.) | $(M + H)^+$ |
|---|---|---|---|---|---|
| E-17 | | D-13 | isopropyl hydrazine | 1.73 | 372 |
| E-18 | | D-13 | cyclopentyl hydrazine | 1.94 | 398 |
| E-19 | | D-13 | cyclohexyl hydrazine | 2.00 | 412 |
| E-20 | | D-13 | tert-butyl hydrazine | 1.86 | 386 |
| E-21 | | D-13 | ethyl hydrazine | 1.61 | 358 |
| E-22 | | D-13 | methyl hydrazine | 1.57 | 344 |

TABLE 3-continued

Examples E01-E42

| No. | MOLSTRUCTURE | Diketone | Hydrazine | $t_R$ (min.) | $(M + H)^+$ |
|---|---|---|---|---|---|
| E-23 | | D-15 | isopropyl hydrazine | | 253 |
| E-24 | | D-15 | isopropyl hydrazine | 1.66 | 295 |
| E-25 | | D-15 | cyclohexyl hydrazine | 1.96 | 335 |
| E-26 | | D-15 | methyl hydrazine | 1.37 | 267 |
| E-27 | | D-15 | cyclobutyl hydrazine | 1.78 | 307 |
| E-28 | | D-17 | isopropyl hydrazine | 1.73 | 311 |

TABLE 3-continued

Examples E01-E42

| No. | MOLSTRUCTURE | Diketone | Hydrazine | $t_R$ (min.) | $(M + H)^+$ |
|---|---|---|---|---|---|
| E-29 | | D-17 | cyclopentyl hydrazine | 1.99 | 337 |
| E-30 | | D-14 | cyclohexyl hydrazine | 2.08 | 426 |
| E-31 | | D-14 | 2-chloro phenyl hydrazine | 1.94 | 454/456 |
| E-32 | | D-14 | methyl hydrazine | 1.66 | 358 |
| E-33 | | D-14 | o-tolyl hydrazine | 1.97 | 434 |
| E-34 | | D-14 | phenyl hydrazine | 1.94 | 420 |

TABLE 3-continued

Examples E01-E42

| No. | MOLSTRUCTURE | Diketone | Hydrazine | $t_R$ (min.) | $(M + H)^+$ |
|---|---|---|---|---|---|
| E-35 | | D-14 | 3-chloro-4-hydrazino-N,N-dimethyl-benzamide | 1.78 | 525 |
| E-36 | | D-14 | tert-butyl hydrazine | 1.84 | 400 |
| E-37 | | D-17 | cyclohexyl hydrazine | 2.05 | 351 |
| E-38 | | D-17 | cyclobutyl hydrazine | 1.87 | 323 |
| E-39 | | D-17 | methyl hydrazine | 1.45 | 283 |

TABLE 3-continued

Examples E01-E42

| No. | MOLSTRUCTURE | Diketone | Hydrazine | $t_R$ (min.) | $(M + H)^+$ |
|---|---|---|---|---|---|
| E-40 | | D-06 | 4-hydrazino-cyclohexanecarboxylic acid ethyl ester | 1.22 | 468 |
| E-41 | | D-07 | 4-hydrazino-cyclohexanecarboxylic acid ethyl ester | 1.43 | 498 |
| E-42 | | D-05 | 4-hydrazino-cyclohexanecarboxylic acid ethyl ester | 1.44 | 431 |

Examples F

Examples F-01 to F-04 are synthesized according to the following general procedure. The appropriate starting material required for synthesis can be deduced from the table of examples.

General Procedure F

A mixture of corresponding ester (1.00 mmol) and lithium hydroxide mono hydrate (10.0 mmol) in 20 mL THF and 5 mL water is stirred at over night at RT. The reaction mixture is acidified with acetic acid and diluted with water. THF is evaporated under reduced pressure. The precipitated product is filtered off, washed with water and used without further purification in the next step.

TABLE 4

Examples F01-F04

| No. | MOLSTRUCTURE | Starting material | $t_R$ (min.) | $(M + H)^+$ |
|---|---|---|---|---|
| F-01 | | E-15 | 2.24 | 486/470 |
| F-02 | | E-40 | 1.08 | 440 |
| F-03 | | E-41 | 1.23 | 470 |
| F-04 | | E-42 | 1.21 | 403 |

Examples G

Examples G-01 to G-09 are synthesized according to the following general procedure G. The appropriate starting materials required for the synthesis can be deduced from the table of examples.

General Procedure G

The corresponding acid (1 eq.) is taken up in DMA or DMF, DIPEA (4 eq.) and HATU (1.3 eq.) are added and the reaction mixture is stirred for 10 min at RT. Amine is added and the reaction mixture is stirred overnight at RT followed by 1 h at 55° C. if necessary. The desired product is either precipitated from the reaction mixture or aqueous potassium carbonate solution is added and the resultant mixture is extracted with DCM and purified by HPLC (C18, 5-98% acetonitrile in water containing 0.1% formic acid or MeOH/water and TFA).

TABLE 5

Examples G01-G09

| No. | MOLSTRUCTURE | Acid | Amine | $t_R$ (min.) | $(M + H)^+$ |
|---|---|---|---|---|---|
| G-01 | | F-01 | 4-pyrrolidin-1-yl-cyclohexylamine | | 618/620 |
| G-02 | | F-04 | dimethyl amine | 1.22 | 430 |
| G-03 | | F-04 | methyl-(4-pyrrolidin-1-yl-cyclohexyl)-amine | 1.18 | 567 |

TABLE 5-continued
Examples G01-G09
| No. | MOLSTRUCTURE | Acid | Amine | t_R (min.) | (M + H)+ |
|---|---|---|---|---|---|
| G-04 | 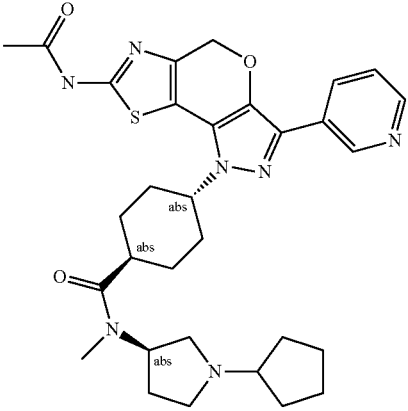 Chiral | F-02 | ((R)-1-Cyclopentyl-pyrrolidin-3-yl)-methyl-amine | 1.08 | 590 |
| G-05 | 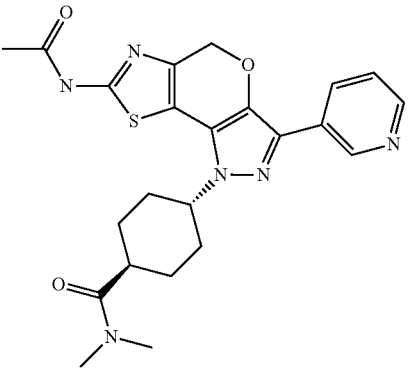 [SMILES: CC(=O)Nc1nc2c(s1)-c1c(c(-c3cccnc3)nn1[C@H]1CC[C@H](C(=O)N(C)C)CC1)OC2] | F-02 | dimethyl amine | 1.09 | 467 |
| G-06 | 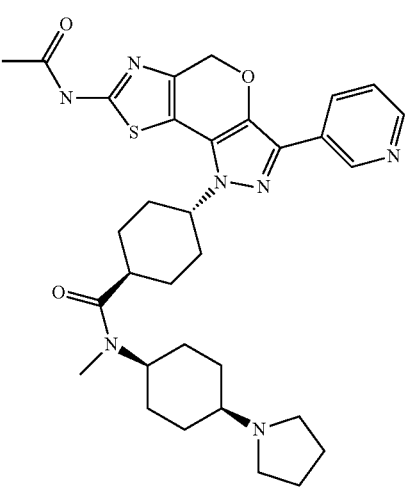 [SMILES: CC(=O)Nc1nc2c(s1)-c1c(c(-c3cccnc3)nn1[C@H]1CC[C@H](C(=O)N(C)[C@H]3CC[C@@H](N4CCCC4)CC3)CC1)OC2] | F-02 | Methyl-(4-pyrrolidin-1-yl cyclohexyl)-amine | 1.06 | 604 |

TABLE 5-continued

Examples G01-G09

| No. | MOLSTRUCTURE | Acid | Amine | $t_R$ (min.) | $(M + H)^+$ |
|---|---|---|---|---|---|
| G-07 | | F-03 | Methyl-(4-pyrrolidin-1-yl-cyclohexyl)-amine | | 634 |
| G-08 | | F-03 | Methyl-(4-pyrrolidin-1-yl-cyclohexyl)-amine | | |
| G-09 | | F-03 | Methyl-(4-methyl-4-pyrrolidin-1-yl-cyclohexyl)-amine | | 648 |

Analytical Method 1

| HPLC: | Agilent 1100 Series |
|---|---|
| MS: | Agilent LC/MSD SL |
| column: | Phenomenex, Mercury Gemini C18, 3 µm, 2.0 × 20 mm, Part.No. 00M-4439-B0-CE |

| | | | |
|---|---|---|---|
| solvent | A: | 5 mM NH₄HCO₃/ 20 mM NH₃ | |
| | B: | acetonitrile HPLC grade | |
| detection: | MS: | Positive and negative | |
| | mass range: | 120-700 m/z | |
| | fragmentor: | 70 | |
| | gain EMV: | 1 | |
| | threshold: | 150 | |
| | stepsize: | 0.25 | |
| | UV: | 315 nm | |
| | bandwidth: | 170 nm | |
| | reference: | off | |
| | range: | 210-400 nm | |
| | range step: | 2.00 nm | |
| | peakwidth: | <0.01 min | |
| | slit: | 2 nm | |
| injection: | 5 µL | | |
| flow: | 1.00 mL/min | | |
| column temperature: | 40° C. | | |
| gradient: | | 0.00 min | 5% B |
| | | 0.00-2.50 min | 5% -> 95% B |
| | | 2.50-2.80 min | 95% B |
| | | 2.81-3.10 min | 95% -> 5% B |

Abbreviations Used

| | | | |
|---|---|---|---|
| bu | butyl | tert | tertiary |
| d | day(s) | THF | tetrahydrofuran |
| DC | thin layer chromatography | LiHMDS | Lithium hexamethyl disilazide |
| DCM | dichloromethane | iPr | isopropyl |
| DMF | N,N-dimethylformamide | MTBE | tertiary butylmethylether |
| DMSO | dimethylsulphoxide | NP | normal phase |
| et | ethyl | CDI | carbonyl diimidazole |
| h | hour(s) | ACN | acetonitrile |
| HPLC | high performance liquid chromatography | BINAP | 2R,3S,2,2'-bis-(diphenyl-phosphino)-1,1'-binapthyl |
| M | molar | DIPEA | diisopropylethyl amine |
| me | methyl | | |
| min | minute(s) | DCE | 1,2-dichloroethane |
| mL | milliliter | NMP | N-methylpyrrolindinone |
| MS | mass spectrometry | prep | preparative |
| N | normal | conc. | concentrated |
| NMR | nuclear resonance spectroscopy | TFA | trifluoroacetic acid |
| ppm | part per million | HATU | N-[(dimethylamino)-(1H-1,2,3-triazolo[4,5-b]pyridin-1-yl)-methylene]-N-methylmethan-aminium hexafluorophosphate N-oxide |
| $R_f$ | retention factor | DMA | N,N-dimethylacetamide |
| RP | reversed phase | TBTU | O-(Benzotriazol-1-yl)-N,N,N',N'-tetramethyluronium tetrafluoroborate |
| RT | room temperature | PEPPSI | [1,3-Bis(2,6-Diisopropylphenyl)-imidazol-2-ylidene](3-chloro-pyridyl) palladium(II) dichloride |
| $t_R$ | retention time | m.p. | melting point |
| DMAP | dimethyl-pyridin-4-yl-amine | DBU | 1,8-diazabicyclo[5.4.0]undec-7-ene |

The Examples that follow describe the biological activity of the compounds according to the invention without restricting the invention to these Examples.

PC3 Proliferation Test

The test is based on measurement of cellular DNA content via fluorescent dye binding. Because cellular DNA content is highly regulated, it is closely proportional to cell number. The extent of proliferation is determined by comparing cell counts for samples treated with drugs with untreated controls.

PC3 (human prostate carcinoma cell line) cells are sown in microtitre plates and incubated overnight in culture medium at 37° C. and 5% $CO_2$. The test substances are diluted stepwise and added to the cells such that the total volume is 200 µL/well. Cells to which diluent, but not substance, is added serve as controls. After an incubation time of 3 days, the medium is replaced by 100 µL/well dye-binding solution and the cells are incubated at 37° C. in the dark for a further 60 min. For measuring the fluorescence, excitation takes place at a wavelength of 485 nm and the emission is measured at 530 nm.

$EC_{50}$ values are calculated using the GraphPad Prism program.

Most compounds of the Examples cited have an $EC_{50}$ (Proliferation PC3) of less than 5.0 µM.

P-AKT Measurement in PC3 Cells

P-AKT levels in PC3 cells are detected by cell-based ELISA. Cells are cultured in 96-well plates and treated with serial dilutions of test substances for 2 h. Cells to which diluent, but not substance, is added serve as controls. Subsequently, the cells are fixed rapidly to pre-serve protein modifications. Each well is then incubated with a primary antibody specific for Ser473-phosphorylated AKT. Subsequent incubation with secondary HRP-conjugated antibody and developing solution provides a colorimetric readout at 450 nm.

$EC_{50}$ values are calculated using the GraphPad Prism program.

Most compounds of the Examples cited have an $EC_{50}$ (P-AKT PC3) of less than 1.0 µM.

The substances of the present invention are PI3 kinase inhibitors. On account of their biological properties, the novel compounds of the general formula (1) and their isomers and their physiologically tolerated salts are suitable for treating diseases which are characterized by excessive or anomalous cell proliferation.

These diseases include, for example: viral infections (e.g. HIV and Kaposi's sarcoma); inflammation and autoimmune diseases (e.g. colitis, arthritis, Alzheimer's disease, glomerulonephritis and wound healing); bacterial, fungal and/or parasitic infections; leukaemias, lymphomas and solid tumours; skin diseases (e.g. psoriasis); bone diseases; cardiovascular diseases (e.g. restenosis and hypertrophy). In addition, the compounds are useful for protecting proliferating cells (e.g. hair cells, intestinal cells, blood cells and progenitor cells) from DNA damage due to irradiation, UV treatment and/or cytostatic treatment (Davis et al., 2001).

For example, the following cancers may be treated with compounds according to the invention, without being restricted thereto:

brain tumours such as for example acoustic neurinoma, astrocytomas such as fibrillary, protoplasmic, gemistocytary, anaplastic, pilocytic astrocytomas, glioblastoma, gliosarcoma, pleomorphic xanthoastrocytoma, subependymal large-cell giant cell astrocytoma and desmoplastic infantile astrocytoma; brain lymphomas, brain metastases, hypophyseal tumour such as prolactinoma, hypophyseal incidentaloma, HGH (human growth hormone) producing adenoma and corticotrophic adenoma, craniopharyngiomas, medulloblastoma, meningeoma and oligodendroglioma; nerve tumours such as for example tumours of the vegetative nervous system such as neuroblastoma, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus and duodenum; eyelid tumours (basalioma or adenocarcinoma of the eyelid apparatus); retinoblastoma; carcinoma of the pancreas; carcinoma of the bladder; lung tumours (bronchial carcinoma-small-cell lung cancer (SCLC), non-small-cell lung cancer (NSCLC) such as for example spindle-cell plate epithelial carcinomas, adenocarcinomas (acinary, paillary, bronchiolo-alveolar) and large-cell bronchial carcinoma (giant cell carcinoma, clear-cell carcinoma)); breast cancer such as ductal, lobular, mucinous or tubular carcinoma, Paget's carcinoma; non-Hodgkin's lymphomas (B-lymphatic or T-lymphatic NHL) such as for example hair cell leukaemia, Burkitt's lymphoma or mucosis fungoides; Hodgkin's disease; uterine cancer (corpus carcinoma or endometrial carcinoma); CUP syndrome (Cancer of Unknown Primary); ovarian cancer (ovarian carcinoma—mucinous or serous cystoma, endometriodal tumours, clear cell tumour, Brenner's tumour); gall bladder cancer; bile duct cancer such as for example Klatskin tumour; testicular cancer (germinal or non-germinal germ cell tumours); laryngeal cancer such as for example supraglottal, glottal and subglottal tumours of the vocal cords; bone cancer such as for example osteochondroma, chondroma, chondroblastoma, chondromyxoid fibroma, chondrosarcoma, osteoma, osteoid osteoma, osteoblastoma, osteosarcoma, non-ossifying bone fibroma, osteofibroma, desmoplastic bone fibroma, bone fibrosarcoma, malignant fibrous histiocyoma, osteoclastoma or giant cell tumour, Ewing's sarcoma, and plasmocytoma, head and neck tumours (HNO tumours) such as for example tumours of the lips, and oral cavity (carcinoma of the lips, tongue, oral cavity), nasopharyngeal carcinoma (tumours of the nose, lymphoepithelioma), pharyngeal carcinoma, oropharyngeal carcinomas, carcinomas of the tonsils (tonsil malignoma) and (base of the) tongue, hypopharyngeal carcinoma, laryngeal carcinoma (cancer of the larynx), tumours of the paranasal sinuses and nasal cavity, tumours of the salivary glands and ears; liver cell carcinoma (hepatocellular carcinoma (HCC); leukaemias, such as for example acute leukaemias such as acute lymphatic/lymphoblastic leukaemia (ALL), acute myeloid leukaemia (AML); chronic lymphatic leukaemia (CLL), chronic myeloid leukaemia (CML); stomach cancer (papillary, tubular or mucinous adenocarcinoma, adenosquamous, squamous or undifferentiated carcinoma; malignant melanomas such as for example superficially spreading (SSM), nodular (NMM), lentigo-maligna (LMM), acral-lentiginous (ALM) or amelanotic melanoma (AMM); renal cancer such as for example kidney cell carcinoma (hypernephroma or Grawitz's tumour); oesophageal cancer; penile cancer; prostate cancer; vaginal cancer or vaginal carcinoma; thyroid carcinomas such as for example papillary, follicular, medullary or anaplastic thyroid carcinoma; thymus carcinoma (thymoma); cancer of the urethra (carcinoma of the urethra, urothelial carcinoma) and cancer of the vulva.

The novel compounds can be used for the prevention or short-term or long-term treatment of the abovementioned diseases including, where appropriate, in combination with other state-of-the-art compounds such as other anti-tumour substances, cytotoxic substances, cell proliferation inhibitors, antiangiogenic substances, steroids or antibodies.

The compounds of the general formula (1) can be used on their own or in combination with other active compounds according to the invention and, where appropriate, in combination with other pharmacologically active compounds as well. Chemotherapeutic agents which can be administered in combination with the compounds according to the invention include, without being restricted thereto, hormones, hormone analogs and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone and octreotide), aromatase inhibitors (e.g. anastrozole, letrozole, liarozole, vorozole, exemestane and atamestane), LHRH agonists and antagonists (e.g. goserelin acetate and luprolide), inhibitors of growth factors (growth factors such as platelet-derived growth factor and hepatocyte growth factor, examples of inhibitors are growth factor antibodies, growth factor receptor antibodies and tyrosine kinase inhibitors, such as gefitinib, imatinib, lapatinib, Erbitux® and trastuzumab); antimetabolites (e.g. antifolates such as methotrexate and raltitrexed, pyrimidine analogs such as 5-fluorouracil, capecitabine and gemcitabine, purine and adenosine analogs such as mercaptopurine, thioguanine, cladribine and pentostatin, cytarabine and fludarabine); antitumour antibiotics (e.g. anthracyclines, such as doxorubicin, daunorubicin, epirubicin and idarubicin, mitomycin C, bleomycin, dactinomycin, plicamycin and streptozocin); platinum derivatives (e.g. cisplatin, oxaliplatin and carboplatin); alkylating agents (e.g. estramustine, meclorethamine, melphalan, chlorambucil, busulphan, dacarbazine, cyclophosphamide, ifosfamide and temozolomide, nitrosoureas such as carmustine and lomustine and thiotepa); antimitotic agents (e.g. vinca alkaloids such as vinblastine, vindesine, vinorelbine and vincristine; and taxans such as paclitaxel and docetaxel); topoisomerase inhibitors (e.g. epipodophyllotoxins such as etoposide and etopophos, teniposide, amsacrine, topotecan, irinotecan and mitoxantrone) and various chemotherapeutic agents such as amifostin, anagrelide, clodronate, filgrastin, interferon alpha, leucovorin, rituximab, procarbazine, levamisole, mesna, mitotan, pamidronate and porfimer.

Examples of suitable forms for use are tablets, capsules, suppositories, solutions, in particular solutions for injection (s.c., i.v., i.m.) and infusion, syrups, emulsions or dispersible powders. In this connection, the proportion of the pharmaceutically active compound(s) should in each case be in the range of 0.1-90% by weight, preferably 0.5-50% by weight, of the total composition, that is in quantities which are sufficient to achieve the dosage range which is specified below. If necessary, the doses mentioned can be given several times a day.

Appropriate tablets can be obtained, for example, by mixing the active compound(s) with known auxiliary substances, for example inert diluents, such as calcium carbonate, calcium phosphate or lactose, disintegrants, such as maize starch or alginic acid, binders, such as starch or gelatine, lubricants, such as magnesium stearate or talc, and/or agents for achieving a depot effect, such as carboxymethyl cellulose, cellulose acetate phthalate or polyvinyl acetate. The tablets can also comprise several layers.

Correspondingly, sugar-coated tablets can be produced by coating cores, which have been prepared in analogy with tablets, with agents which are customarily used in sugar coatings, for example collidone or shellac, gum arabic, talc, titanium dioxide or sugar. The core can also comprise several layers in order to achieve a depot effect or to avoid incompatibilities. In the same way, the sugar coating can also comprise several layers in order to achieve a depot effect, with it being possible to use the auxiliary substances which are mentioned above in the case of the tablets.

Syrups of the active compounds or active compound combinations according to the invention can additionally comprise a sweetening agent, such as saccharine, cyclamate, glycerol or sugar as well as a taste-improving agent, e.g. flavouring agents such as vanillin or orange extract. They can also comprise suspension aids or thickeners, such as sodium carboxymethyl cellulose, wetting agents, for example condensation products of fatty alcohols and ethylene oxide, or protectants such as p-hydroxybenzoates.

Injection and infusion solutions are produced in a customary manner, e.g. while adding isotonizing agents, preservatives, such as p-hydroxybenzoates, or stabilizers, such as alkali metal salts of ethylenediaminetetraacetic acid, where appropriate using emulsifiers and/or dispersants, with it being possible, for example, to employ, where appropriate, organic solvents as solubilizing agents or auxiliary solvents when using water as diluent, and aliquoted into injection bottles or ampoules or infusion bottles.

The capsules, which comprise one or more active compounds or active compound combinations, can, for example, be produced by mixing the active compounds with inert carriers, such as lactose or sorbitol, and encapsulating the mixture in gelatine capsules. Suitable suppositories can be produced, for example, by mixing with excipients which are envisaged for this purpose, such as neutral fats or polyethylene glycol, or their derivatives.

Auxiliary substances which may be mentioned by way of example are water, pharmaceutically unobjectionable organic solvents, such as paraffins (e.g. petroleum fractions), oils of vegetable origin (e.g. groundnut oil or sesame oil), monofunctional or poly-functional alcohols (e.g. EtOH or glycerol), carrier substances such as natural mineral powders (e.g. kaolins, argillaceous earths, talc and chalk), synthetic mineral powders (e.g. highly disperse silicic acid and silicates), sugars (e.g. cane sugar, lactose and grape sugar), emulsifiers (e.g. lignin, sulphite waste liquors, methyl cellulose, starch and polyvinyl-pyrrolidone) and glidants (e.g. magnesium stearate, talc, stearic acid and sodium lauryl sulphate).

Administration is effected in a customary manner, preferably orally or transdermally, in particular and preferably orally. In the case of oral use, the tablets can naturally also comprise, in addition to the abovementioned carrier substances, additives such as sodium citrate, calcium carbonate and dicalcium phosphate together with a variety of further substances such as starch, preferably potato starch, gelatine and the like. It is furthermore also possible to use glidants, such as magnesium stearate, sodium lauryl sulphate and talc, for the tableting. In the case of aqueous suspensions, a variety of taste improvers or dyes can also be added to the active compounds in addition to the abovementioned auxiliary substances.

For parenteral administration, it is possible to employ solutions of the active compounds while using suitable liquid carrier materials. The dosage for intravenous administration is 1-1000 mg per hour, preferably between 5 and 500 mg per hour.

Despite this, it may be necessary, where appropriate, to diverge from the above-mentioned quantities, depending on the body weight or the nature of the route of administration, on the individual response to the medicament, on the nature of its formulation and on the time or interval at which the administration is effected. Thus, it may, in some cases, be sufficient to make do with less than the previously mentioned lowest quantity whereas, in other cases, the abovementioned upper limit has to be exceeded. When relatively large quantities are being administered, it may be advisable to divide these into several single doses which are given over the course of the day.

The following formulation examples illustrate the present invention without, however, restricting its scope:

Pharmaceutical Formulation Examples

| A) Tablets | per tablet |
|---|---|
| Active compound in accordance with formula (1) | 100 mg |
| Lactose | 140 mg |
| Maize starch | 240 mg |
| Polyvinylpyrrolidone | 15 mg |
| Magnesium stearate | 5 mg |
| | 500 mg |

The finely ground active compound, lactose and a part of the maize starch are mixed with each other. The mixture is sieved, after which it is moistened with a solution of polyvinyl-pyrrolidone in water, kneaded, wet-granulated and dried. The granular material, the remainder of the maize starch and the magnesium stearate are sieved and mixed with each other. The mixture is pressed into tablets of suitable shape and size.

| B) Tablets | per tablet |
|---|---|
| Active compound in accordance with formula (1) | 80 mg |
| Lactose | 55 mg |
| Maize starch | 190 mg |
| Micro crystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active compound, a part of the maize starch, the lactose, micro-crystalline cellulose and polyvinylpyrrolidone are mixed with each other, after which the mixture is sieved and worked, together with the remainder of the maize starch and water, into a granular material, which is dried and sieved. The sodium carboxymethyl starch and the magnesium stearate are then added to the granular material and mixed with it, and the mixture is pressed into tablets of suitable size.

| C) Ampoule solution | |
|---|---|
| Active compound in accordance with formula (1) | 50 mg |
| Sodium chloride | 50 mg |
| Water for injection | 5 mL |

The active compound is dissolved, either at its intrinsic pH or, where appropriate, at pH 5.5-6.5, in water after which sodium chloride is added as isotonizing agent. The resulting solution is rendered pyrogen-free by filtration and the filtrate is aliquoted, under aseptic conditions, into ampoules, which are then sterilized and sealed by melting. The ampoules contain 5 mg, 25 mg and 50 mg of active compound.

The invention claimed is:

1. A compound selected from the group consisting of:

| No. | MOLSTRUCTURE |
|---|---|
| B1 | 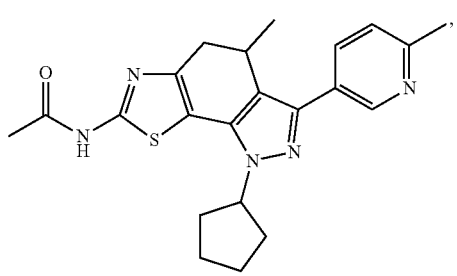 [SMILES: CC(=O)Nc1nc2c(s1)-c1c(c(-c3ccc(C)nc3)nn1C1CCCC1)C(C)C2] |
| B2 | 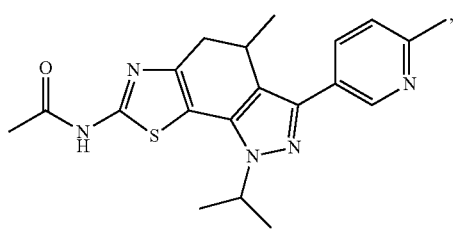 [SMILES: CC(=O)Nc1nc2c(s1)-c1c(c(-c3ccc(C)nc3)nn1C(C)C)C(C)C2] |
| B3 | 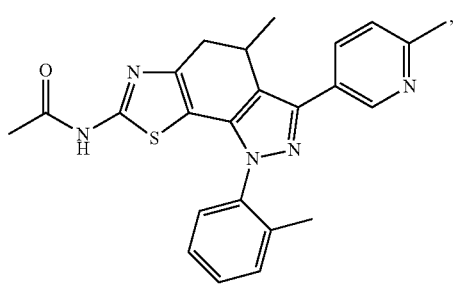 [SMILES: CC(=O)Nc1nc2c(s1)-c1c(c(-c3ccc(C)nc3)nn1-c1ccccc1C)C(C)C2] |
| B4 | 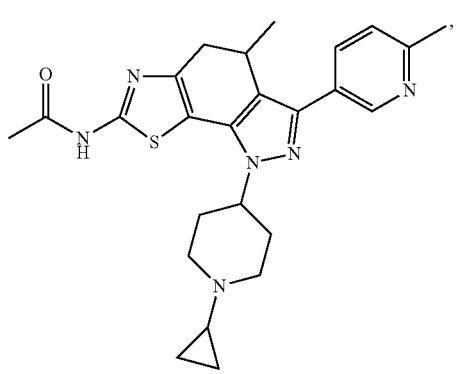 [SMILES: CC(=O)Nc1nc2c(s1)-c1c(c(-c3ccc(C)nc3)nn1C1CCN(C3CC3)CC1)C(C)C2] |
| B5 | 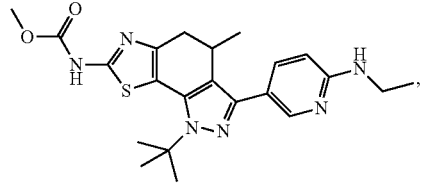 [SMILES: CCNc1ccc(-c2nn(C(C)(C)C)c3c2C(C)Cc2nc(NC(=O)OC)sc2-3)cn1] |
| B6 | 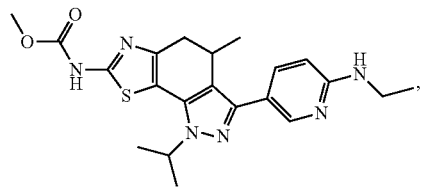 [SMILES: CCNc1ccc(-c2nn(C(C)C)c3c2C(C)Cc2nc(NC(=O)OC)sc2-3)cn1] |
| B7 | 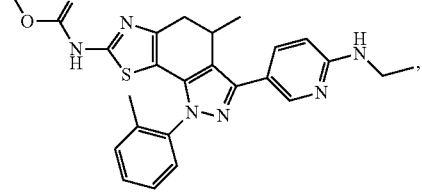 |
| B8 | 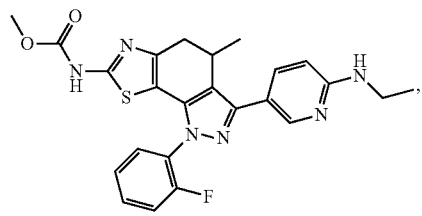 [SMILES: CCNc1ccc(-c2nn(-c3ccccc3F)c3c2C(C)Cc2nc(NC(=O)OC)sc2-3)cn1] |
| B9 | 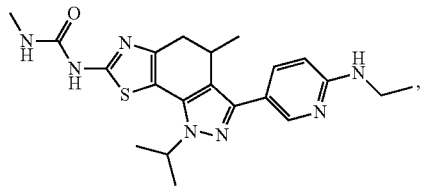 [SMILES: CCNc1ccc(-c2nn(C(C)C)c3c2C(C)Cc2nc(NC(=O)NC)sc2-3)cn1] |
| B10 | 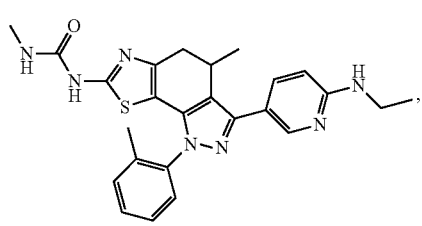 [SMILES: CCNc1ccc(-c2nn(-c3ccccc3C)c3c2C(C)Cc2nc(NC(=O)NC)sc2-3)cn1] |
| B11 | 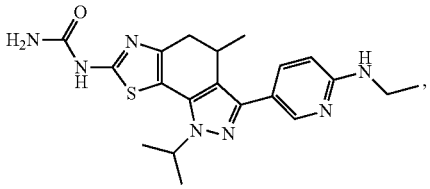 [SMILES: CCNc1ccc(-c2nn(C(C)C)c3c2C(C)Cc2nc(NC(N)=O)sc2-3)cn1] |

| No. | MOLSTRUCTURE |
|---|---|
| B12 | 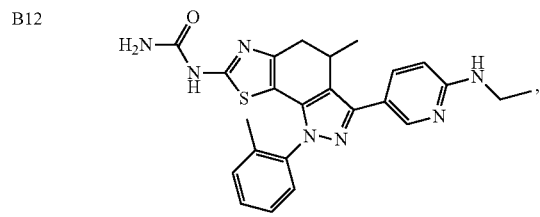 |
| B13 | 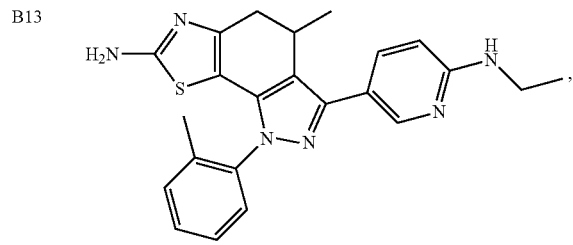 |
| B14 | 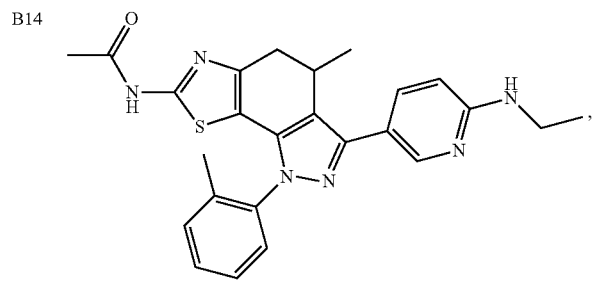 |
| B15 | 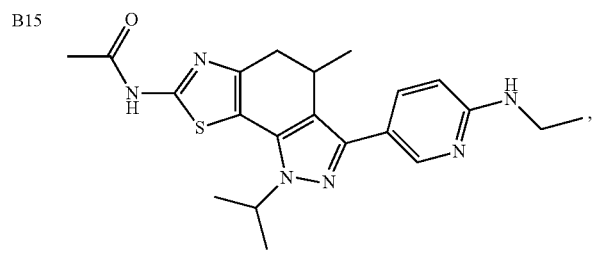 |
| B16 | 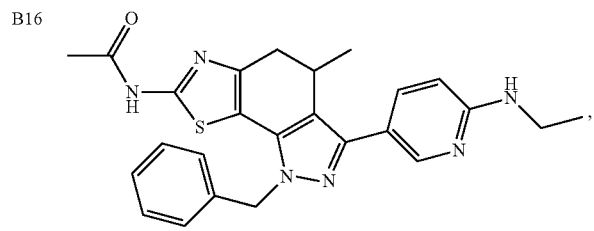 |
| B17 | 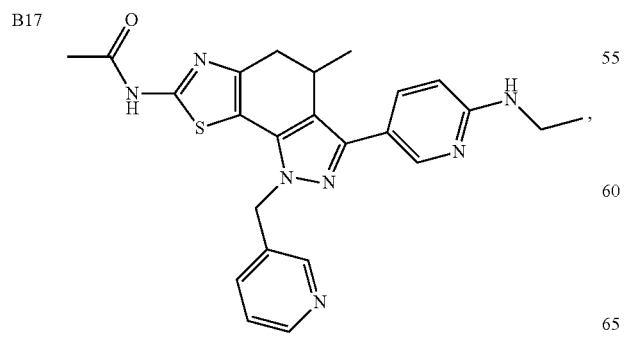 |
| No. | MOLSTRUCTURE |
|---|---|
| B18 | 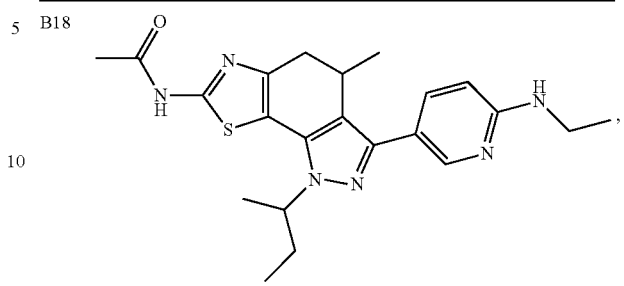 |
| B19 | 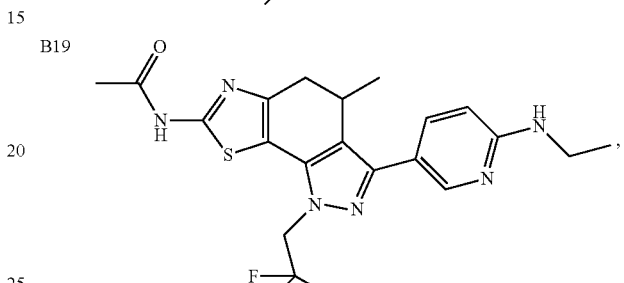 |
| B20 | 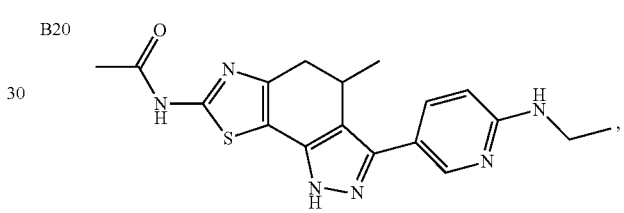 |
| B21 | 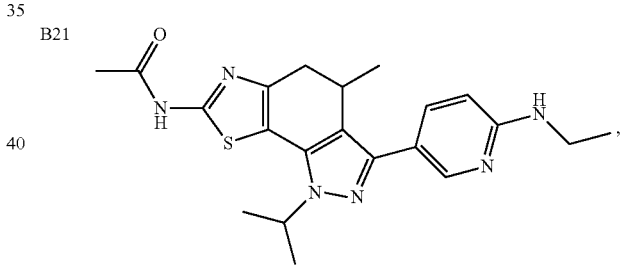 |
| B22 | 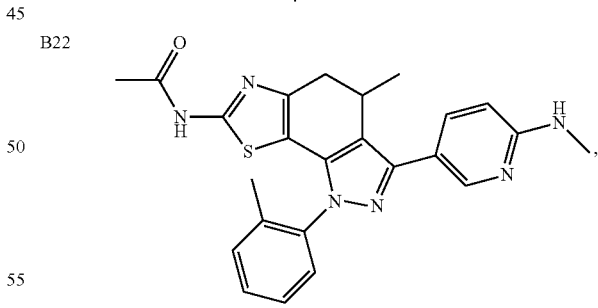 |
| B23 | 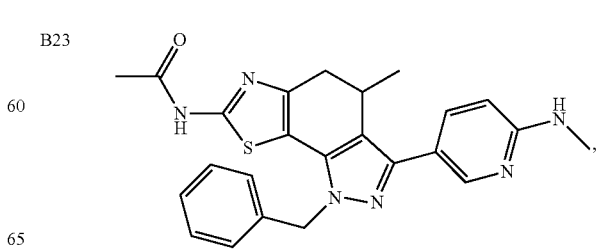 |

| No. | MOLSTRUCTURE |
|---|---|
| B24 | |
| B25 | |
| B26 | |
| B27 | |
| B28 | |

| No. | MOLSTRUCTURE |
|---|---|
| B29 | |
| B30 | |
| B31 | |
| B32 | |
| B33 | |
| B34 | |

|  |  |
| --- | --- |
| No. | MOLSTRUCTURE |
| C1 | 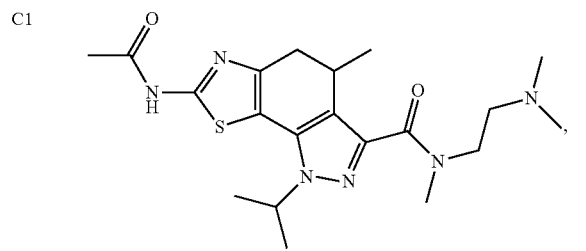 |
| C2 | 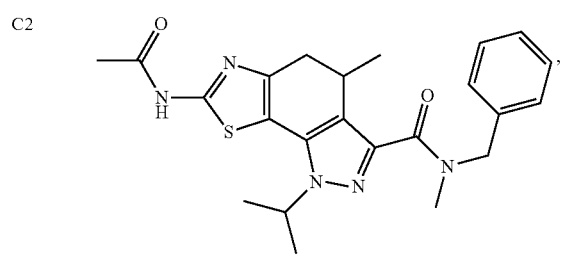 |
| C3 | 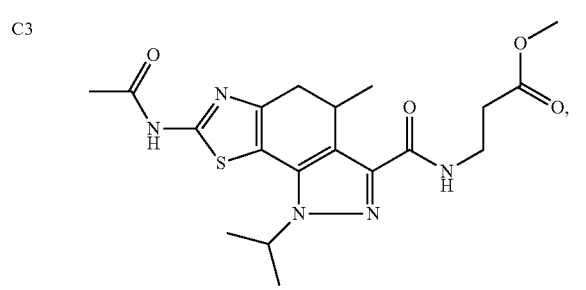 |
| C4 | 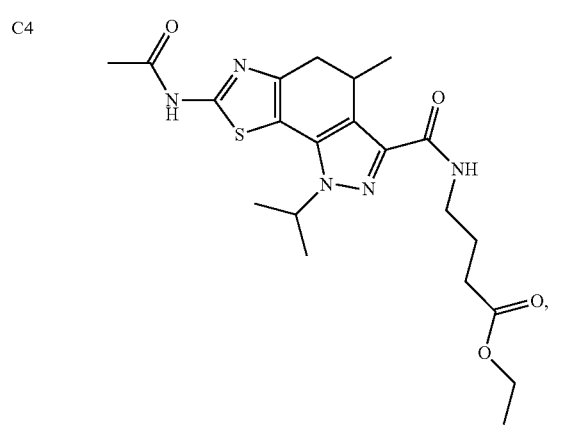 |
| C5 | 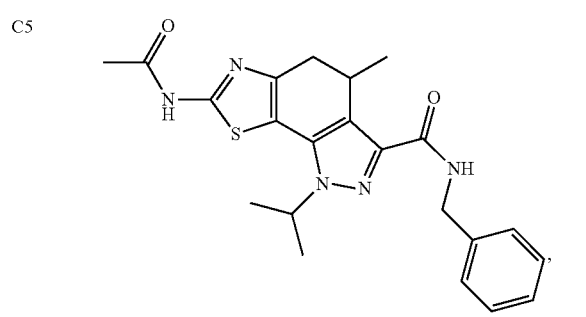 |
|  |  |
| --- | --- |
| No. | MOLSTRUCTURE |
| C6 | 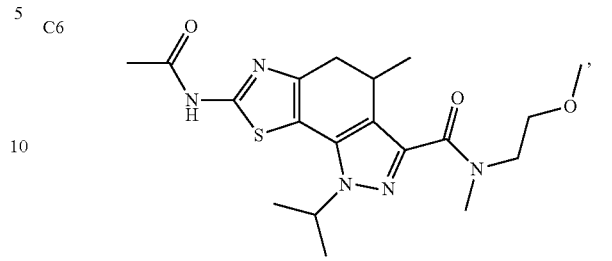 |
| C7 | 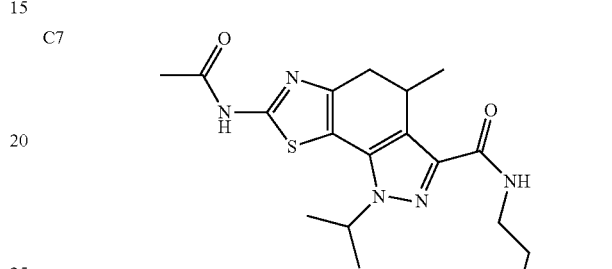 |
| C8 | 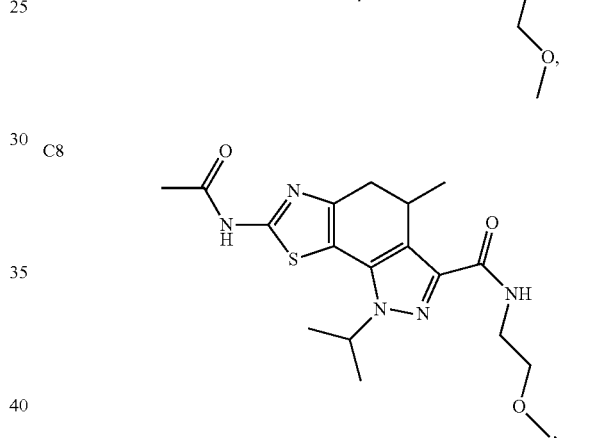 |
| C9 | 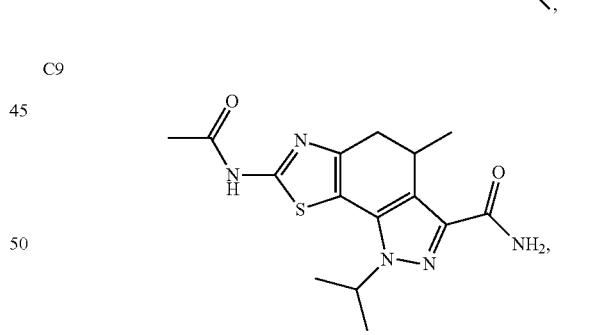 |
| C10 | 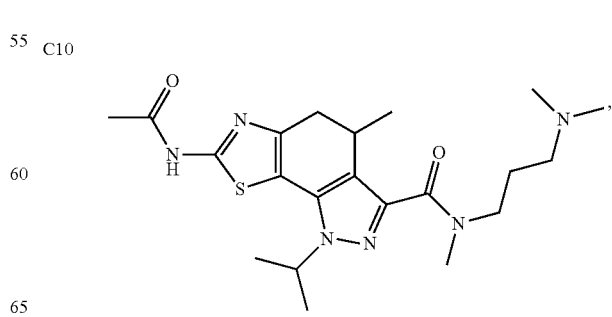 |

| No. | MOLSTRUCTURE |
|---|---|
| C11 | 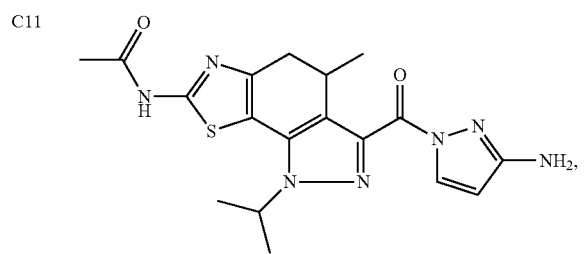 |
| C12 | 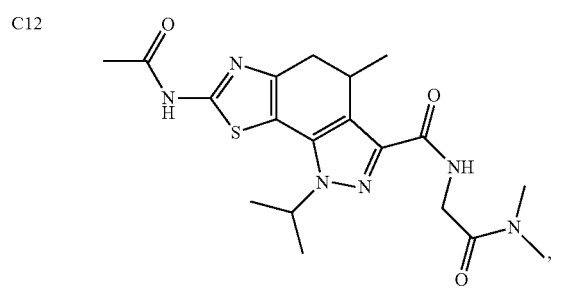 |
| C13 | 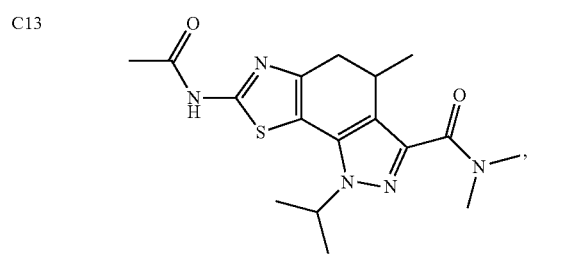 |
| C14 | 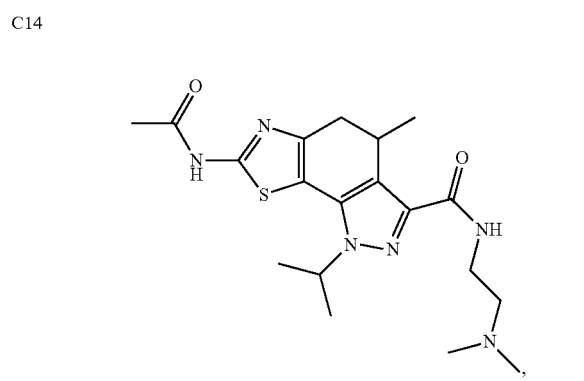 |
| C15 | 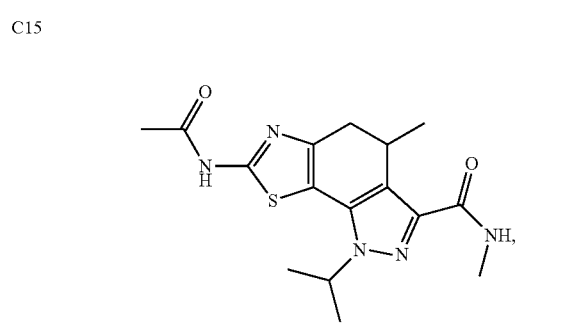 |
| C16 | 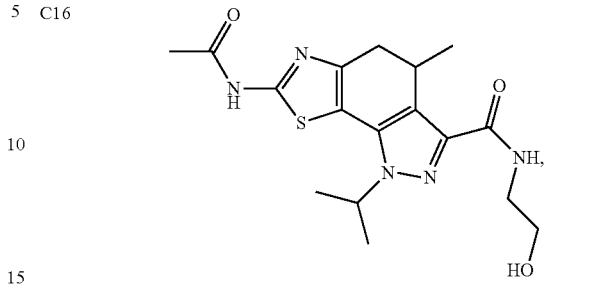 |
| C17 | 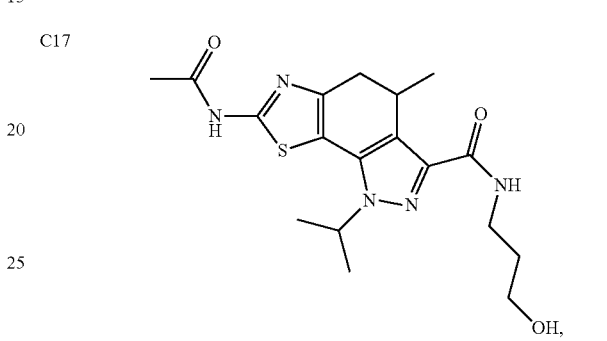 |
| C18 | 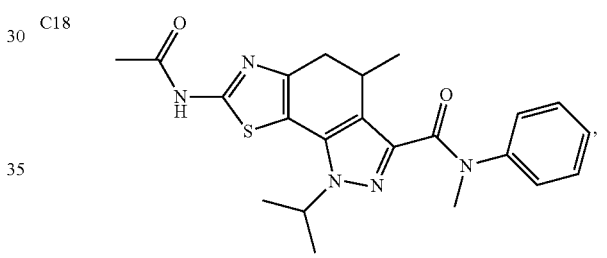 |
| C19 | 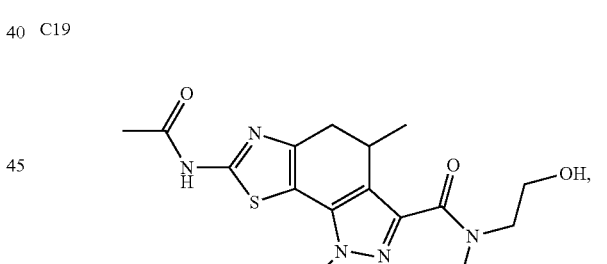 |
| C20 | 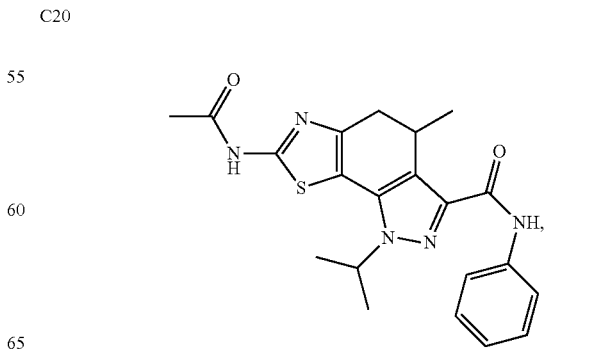 |

| No. | MOLSTRUCTURE |
|---|---|
| C21 | 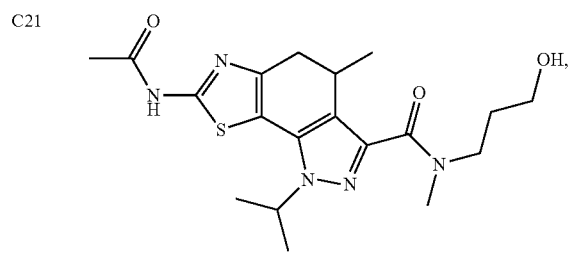 |
| C22 | 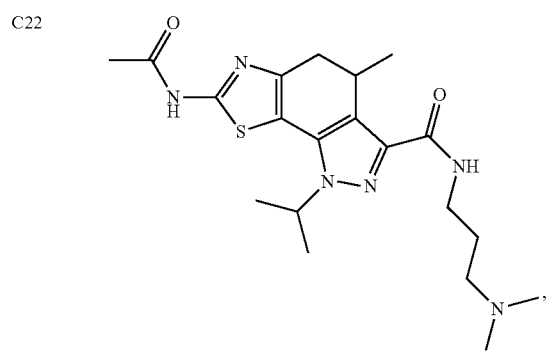 |
| C23 | 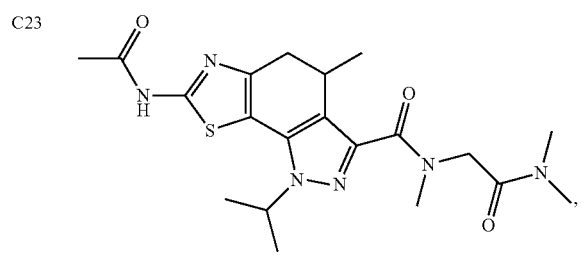 |
| E-01 | 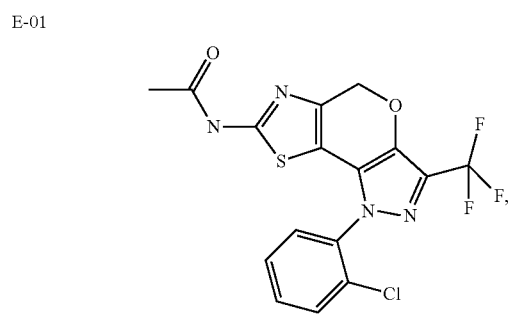 |
| E-02 | 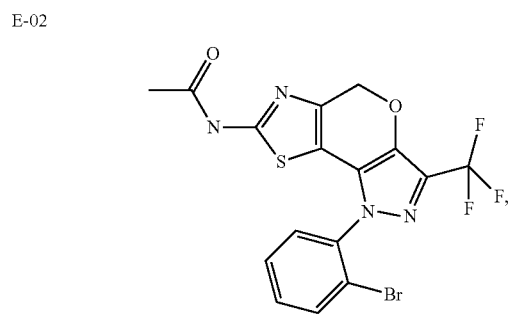 |
| No. | MOLSTRUCTURE |
|---|---|
| E-03 | 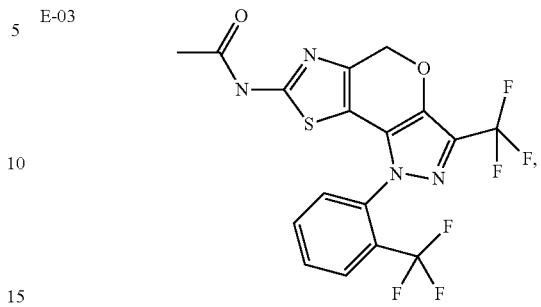 |
| E-04 | 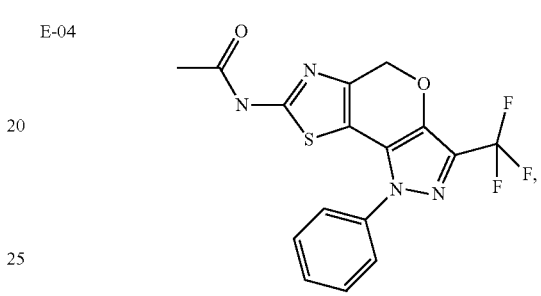 |
| E-05 | 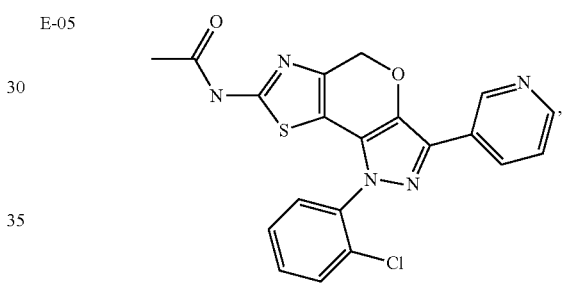 |
| E-06 | 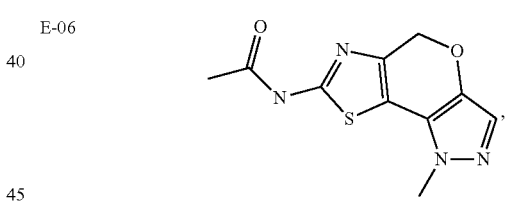 |
| E-07 | 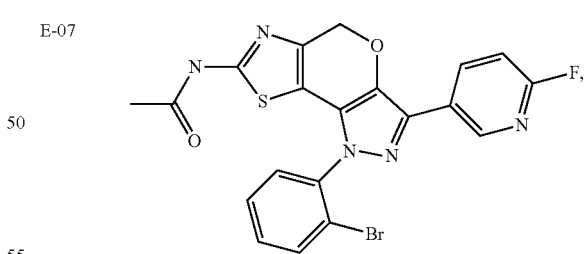 |
| E-08 | 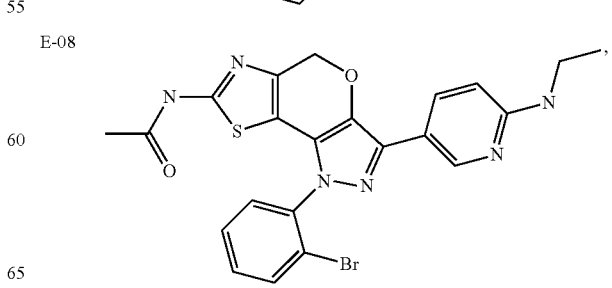 |

| No. | MOLSTRUCTURE |
|---|---|
| E-09 | 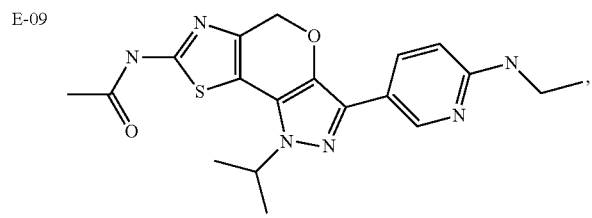 |
| E-10 | 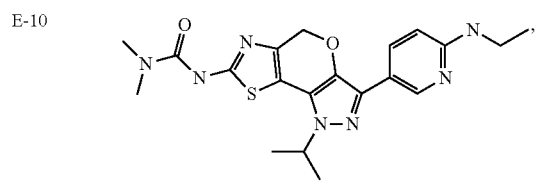 |
| E-11 | 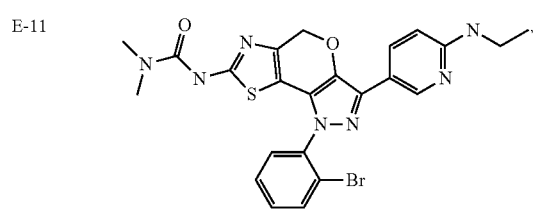 |
| E-12 | 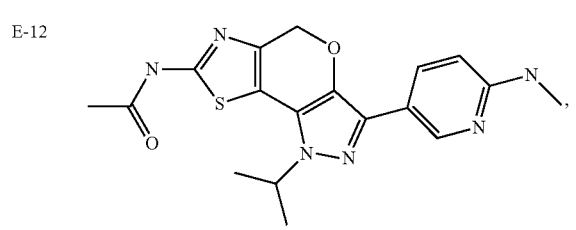 |
| E-13 | 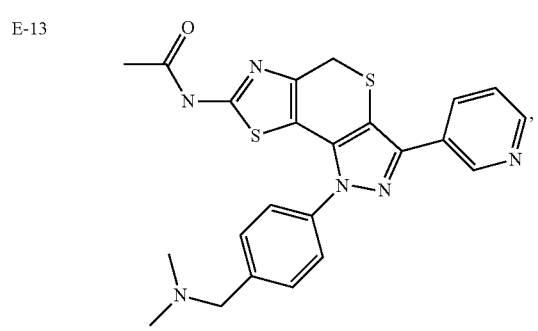 |
| E-14 | 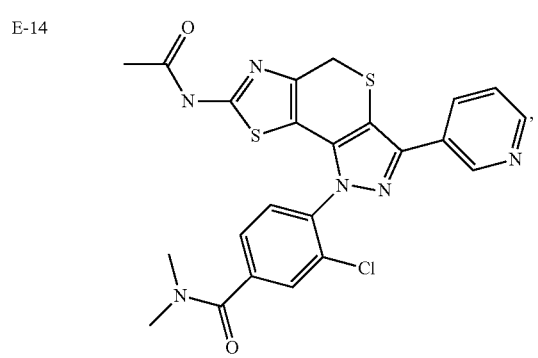 |
| No. | MOLSTRUCTURE |
|---|---|
| E-15 | 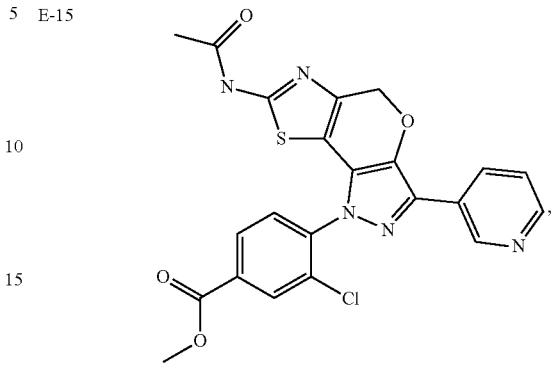 |
| E-16 | 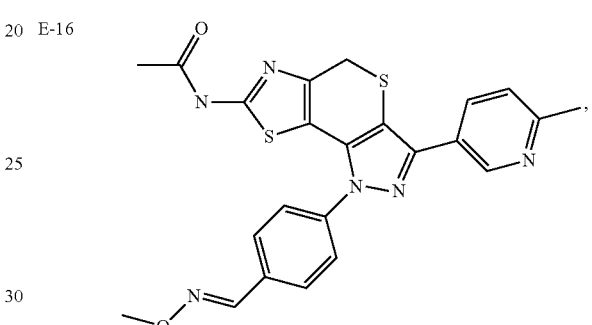 |
| E-17 | 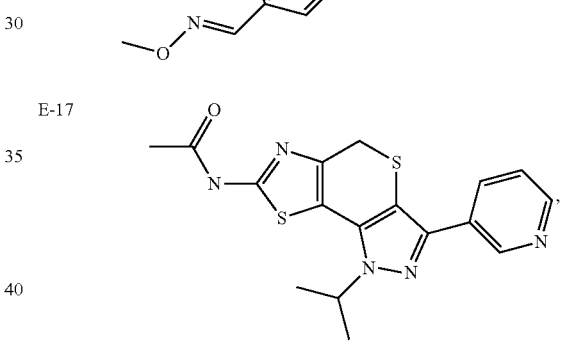 |
| E-18 | 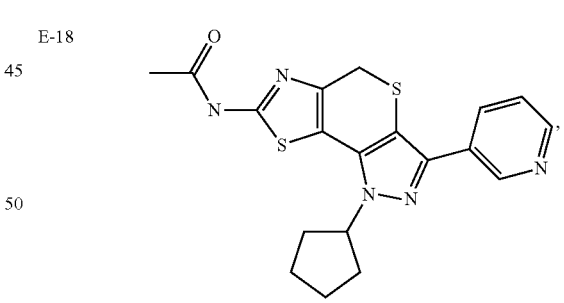 |
| E-19 | 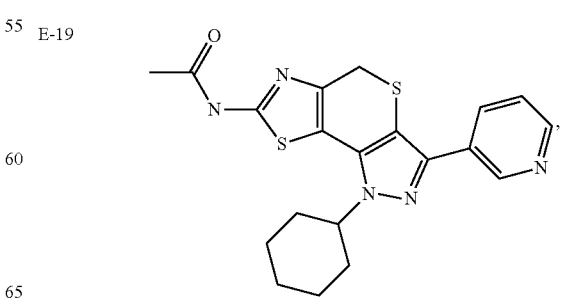 |

| No. | MOLSTRUCTURE |
|---|---|
| E-20 | |
| E-21 | |
| E-22 | |
| E-23 | |
| E-24 | |
| E-25 | |

| No. | MOLSTRUCTURE |
|---|---|
| E-26 | |
| E-27 | |
| E-28 | |
| E-29 | |
| E-30 | |
| E-31 | |

-continued
| No. | MOLSTRUCTURE |
|---|---|
| E-32 | 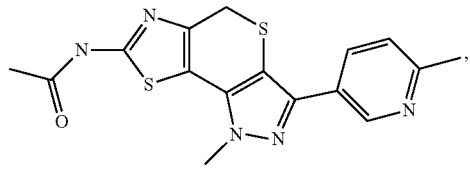 |
| E-33 | 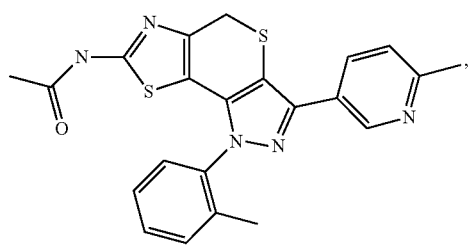 [SMILES: CC(=O)Nc1nc2c(s1)-c1c(c(-c3ccc(C)nc3)nn1-c1ccccc1Cl)SC2] |
| E-34 | 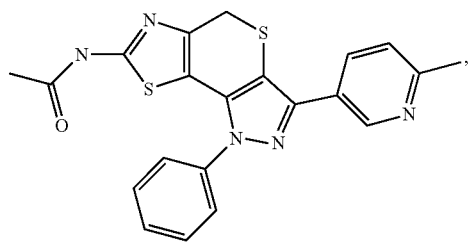 [SMILES: CC(=O)Nc1nc2c(s1)-c1c(c(-c3ccc(C)nc3)nn1-c1ccccc1)SC2] |
| E-35 | 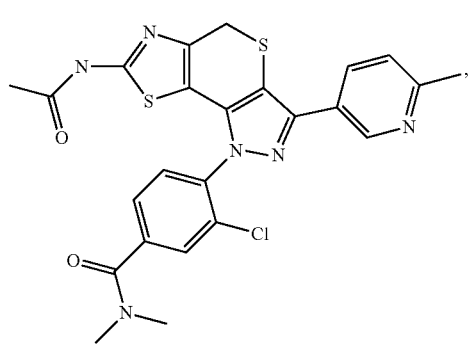 [SMILES: CC(=O)Nc1nc2c(s1)-c1c(c(-c3ccc(C)nc3)nn1-c1ccc(C(=O)N(C)C)cc1Cl)SC2] |
| E-36 | 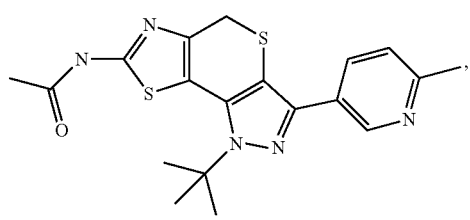 [SMILES: CC(=O)Nc1nc2c(s1)-c1c(c(-c3ccc(C)nc3)nn1C(C)(C)C)SC2] |
| E-37 | 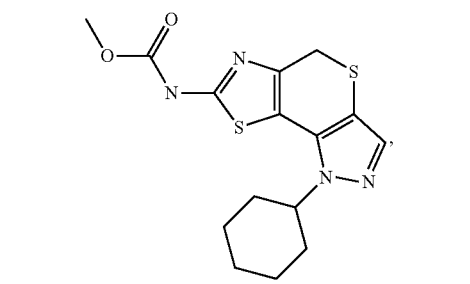 [SMILES: COC(=O)Nc1nc2c(s1)-c1c(cnn1C1CCCCC1)SC2] |
-continued
| No. | MOLSTRUCTURE |
|---|---|
| E-38 | 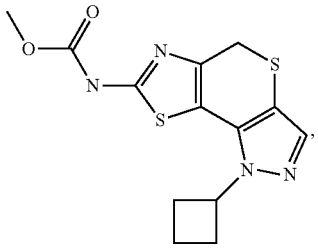 [SMILES: COC(=O)Nc1nc2c(s1)-c1c(cnn1C1CCC1)SC2] |
| E-39 | 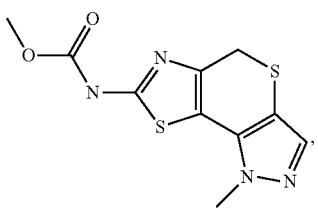 [SMILES: COC(=O)Nc1nc2c(s1)-c1c(cnn1C)SC2] |
| E-40 | 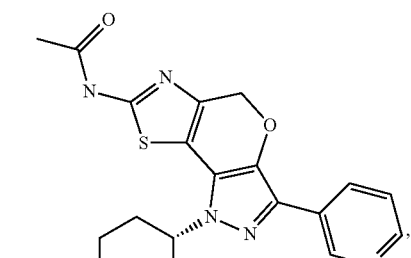 |
| E-41 | 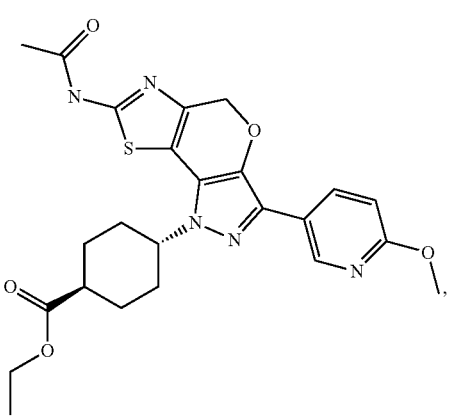 [SMILES: CCOC(=O)[C@H]1CC[C@H](n2nc(-c3ccc(OC)nc3)c3c2-c2sc(NC(C)=O)nc2CO3)CC1] |
| E-42 | 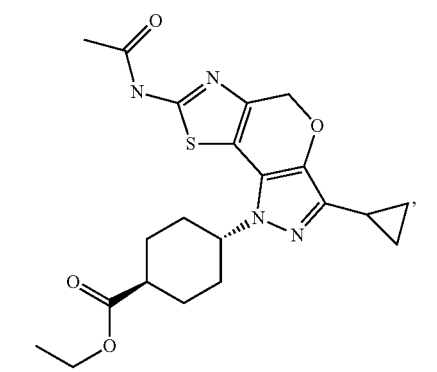 [SMILES: CCOC(=O)[C@H]1CC[C@H](n2nc(C3CC3)c3c2-c2sc(NC(C)=O)nc2CO3)CC1] |

| No. | MOLSTRUCTURE | No. | MOLSTRUCTURE |
|---|---|---|---|
| F-01 | 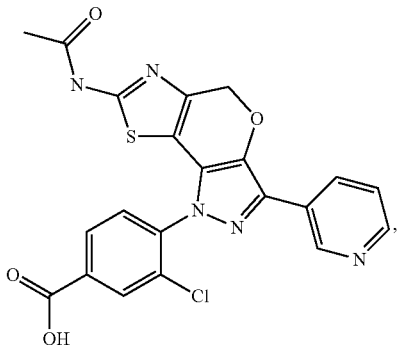 [SMILES: CC(=O)Nc1nc2c(s1)-c1c(c(-c3cccnc3)nn1-c1ccc(C(=O)O)cc1Cl)OC2] | G-01 | 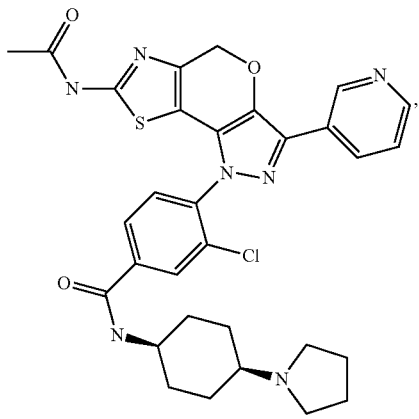 |
| F-02 | 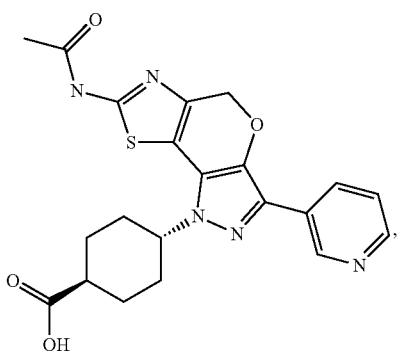 [SMILES: CC(=O)Nc1nc2c(s1)-c1c(c(-c3cccnc3)nn1[C@H]1CC[C@H](C(=O)O)CC1)OC2] | G-02 | 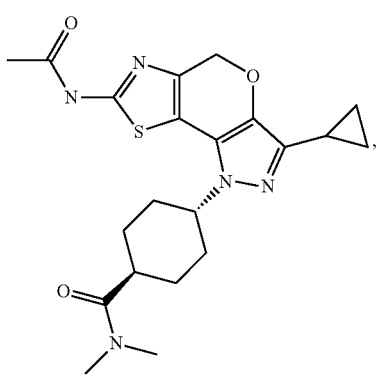 |
| F-03 | 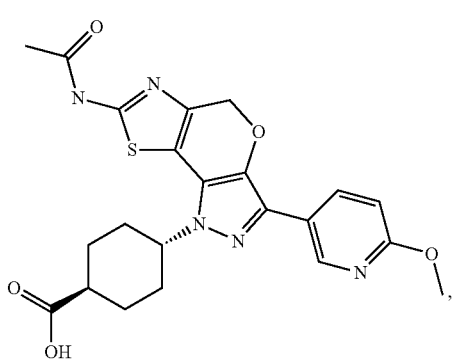 [SMILES: COc1ccc(-c2nn([C@H]3CC[C@H](C(=O)O)CC3)c3c2OCc2nc(NC(C)=O)sc2-3)cn1] | G-03 | 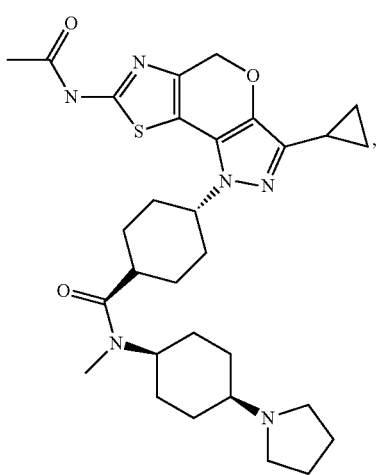 |
| F-04 | 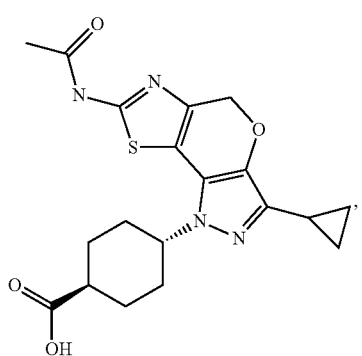 [SMILES: CC(=O)Nc1nc2c(s1)-c1c(c(C3CC3)nn1[C@H]1CC[C@H](C(=O)O)CC1)OC2] | | |

| No. | MOLSTRUCTURE |
|---|---|
| G-04 | 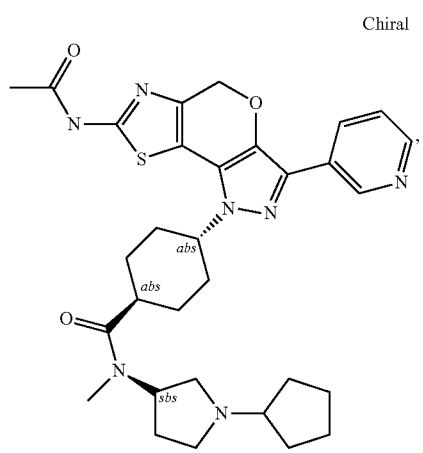 Chiral |
| G-05 | 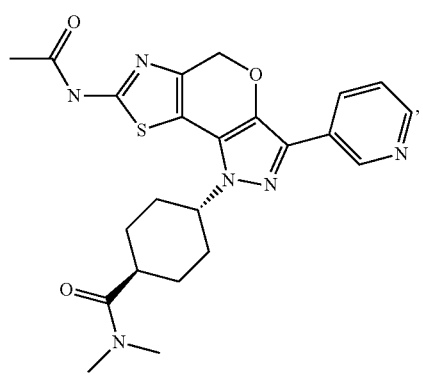 [SMILES: CC(=O)Nc1nc2c(s1)-c1c(c(-c3cccnc3)nn1[C@H]1CC[C@H](C(=O)N(C)C)CC1)OC2] |
| G-06 | 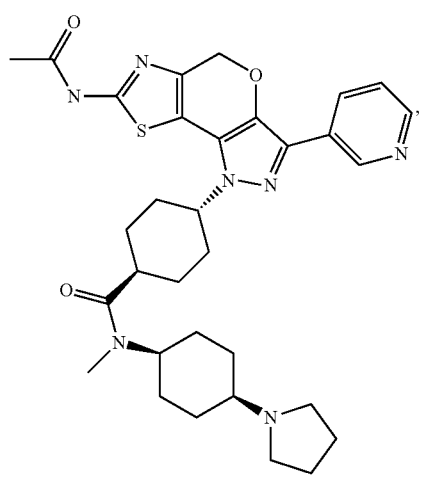 [SMILES: CC(=O)Nc1nc2c(s1)-c1c(c(-c3cccnc3)nn1[C@H]1CC[C@H](C(=O)N(C)[C@H]3CC[C@@H](N4CCCC4)CC3)CC1)OC2] |
| No. | MOLSTRUCTURE |
|---|---|
| G-07 | 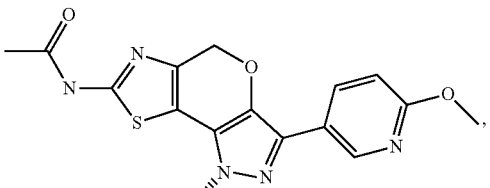 |
| G-08 | 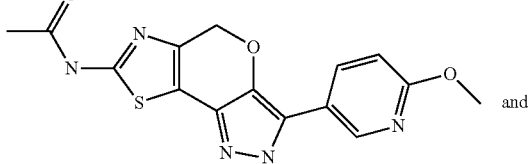 and |
| G-09 | 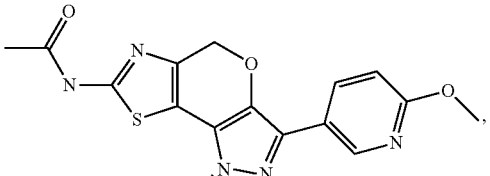 |
or a salt thereof.
2. A pharmacologically acceptable salt of a compound according to claim 1.
3. A pharmaceutical composition comprising a compound according to claim 1, or a pharmacologically acceptable salt thereof and a carrier or excipient.
* * * * *